United States Patent
Nowlin et al.

(12) 
(10) Patent No.: US 8,777,834 B2
(45) Date of Patent: *Jul. 15, 2014

(54) ELASTIC SLING SYSTEM AND RELATED METHODS

(75) Inventors: Brett Nowlin, Bridgewater, MA (US); Michael S. H. Chu, Brookline, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/179,041

(22) Filed: Jul. 8, 2011

(65) Prior Publication Data

US 2011/0263931 A1 Oct. 27, 2011

Related U.S. Application Data

(63) Continuation of application No. 11/429,764, filed on May 8, 2006, now Pat. No. 7,981,023.

(60) Provisional application No. 60/702,539, filed on Jul. 25, 2005, provisional application No. 60/702,540, filed on Jul. 25, 2005, provisional application No. 60/715,362, filed on Sep. 8, 2005.

(51) Int. Cl.
*A61F 2/02* (2006.01)

(52) U.S. Cl.
USPC .......................................................... 600/30

(58) Field of Classification Search
CPC ....... A61F 2/0063; A61F 2/0045; A61F 2/02; A61F 2/04; A61F 2220/0016; A61F 2002/0072; A61B 17/0401; A61B 2017/00805
USPC .......... 600/29, 30, 37; 128/885, 889; 606/139, 606/141, 151, 228; 623/23.72
See application file for complete search history.

(56) References Cited

U.S. PATENT DOCUMENTS

| | | |
|---|---|---|
| 3,003,155 A | 10/1961 | Mielzynski et al. |
| 4,175,557 A | 11/1979 | Hung |
| 5,013,316 A | 5/1991 | Goble et al. |
| 5,197,983 A | 3/1993 | Berman et al. |
| 5,425,740 A | 6/1995 | Hutchinson, Jr. |
| 5,649,937 A | 7/1997 | Bito et al. |
| 5,651,377 A | 7/1997 | O'Donnell, Jr. |
| 5,776,147 A | 7/1998 | Dolendo |
| 5,919,232 A | 7/1999 | Chaffringeon et al. |
| 5,922,026 A | 7/1999 | Chin |
| 5,954,057 A | 9/1999 | Li |

(Continued)

FOREIGN PATENT DOCUMENTS

| | | |
|---|---|---|
| EP | 0677297 | 12/2000 |
| WO | WO 98/35632 | 8/1998 |

(Continued)

OTHER PUBLICATIONS

Kovac, Obstetrics & Gynecology, vol. 89, No. 4, pp. 624-627, Apr. 1997.

*Primary Examiner* — Christine Matthews

(57) ABSTRACT

The invention provides, in various embodiments, systems, devices and methods relating to adjustable length implantable sling assemblies for providing support to anatomical locations. In certain embodiments, the sling includes at least one elastic member to aid in the placement and tensioning of the sling.

20 Claims, 12 Drawing Sheets

(56) References Cited

U.S. PATENT DOCUMENTS

| | | | |
|---|---|---|---|
| 6,042,534 A | 3/2000 | Gellman et al. | |
| 6,042,592 A | 3/2000 | Schmitt | |
| 6,056,688 A | 5/2000 | Benderev et al. | |
| 6,110,101 A | 8/2000 | Tihon et al. | |
| 6,224,616 B1 | 5/2001 | Kugel | |
| 6,452,450 B1 | 9/2002 | Enriguez | |
| 6,475,139 B1 | 11/2002 | Miller | |
| 6,652,450 B2 | 11/2003 | Neisz et al. | |
| 6,666,817 B2 | 12/2003 | Li | |
| 6,689,047 B2 | 2/2004 | Gellman | |
| 6,764,444 B2 | 7/2004 | Wu et al. | |
| 7,083,568 B2 | 8/2006 | Neisz et al. | |
| 7,083,637 B1 | 8/2006 | Tannhauser | |
| 7,981,023 B2 * | 7/2011 | Nowlin et al. | 600/30 |
| 2002/0133236 A1 | 9/2002 | Rousseau | |
| 2002/0183762 A1 | 12/2002 | Anderson et al. | |
| 2003/0114865 A1 | 6/2003 | Sater | |
| 2003/0191360 A1 | 10/2003 | Browning | |
| 2003/0220538 A1 | 11/2003 | Jacquetin | |
| 2004/0004600 A1 | 1/2004 | Yoneno et al. | |
| 2004/0006353 A1 | 1/2004 | Bosley, Jr. et al. | |
| 2004/0039453 A1 | 2/2004 | Anderson et al. | |
| 2004/0106847 A1 | 6/2004 | Benderev | |
| 2004/0144395 A1 | 7/2004 | Evans et al. | |
| 2004/0230092 A1 | 11/2004 | Thierfilder et al. | |
| 2004/0231678 A1 | 11/2004 | Fierro | |
| 2004/0243166 A1 | 12/2004 | Odermatt et al. | |
| 2004/0249240 A1 | 12/2004 | Goldmann et al. | |
| 2004/0249397 A1 | 12/2004 | Delorme et al. | |
| 2004/0267088 A1 | 12/2004 | Kammerer | |
| 2005/0004427 A1 | 1/2005 | Cervigni | |
| 2005/0065395 A1 | 3/2005 | Mellier | |
| 2005/0070829 A1 | 3/2005 | Therin et al. | |
| 2006/0089524 A1 | 4/2006 | Chu | |
| 2006/0089525 A1 | 4/2006 | Mamo et al. | |

FOREIGN PATENT DOCUMENTS

| | | |
|---|---|---|
| WO | WO 02/19945 | 3/2002 |
| WO | WO 02/30293 | 4/2002 |
| WO | WO 03/007847 | 1/2003 |
| WO | WO 03/096928 | 11/2003 |
| WO | WO 2004/016196 | 2/2004 |
| WO | WO 2004/045457 | 6/2004 |
| WO | WO 2005/027786 | 3/2005 |
| WO | WO 2005/094721 | 10/2005 |

* cited by examiner

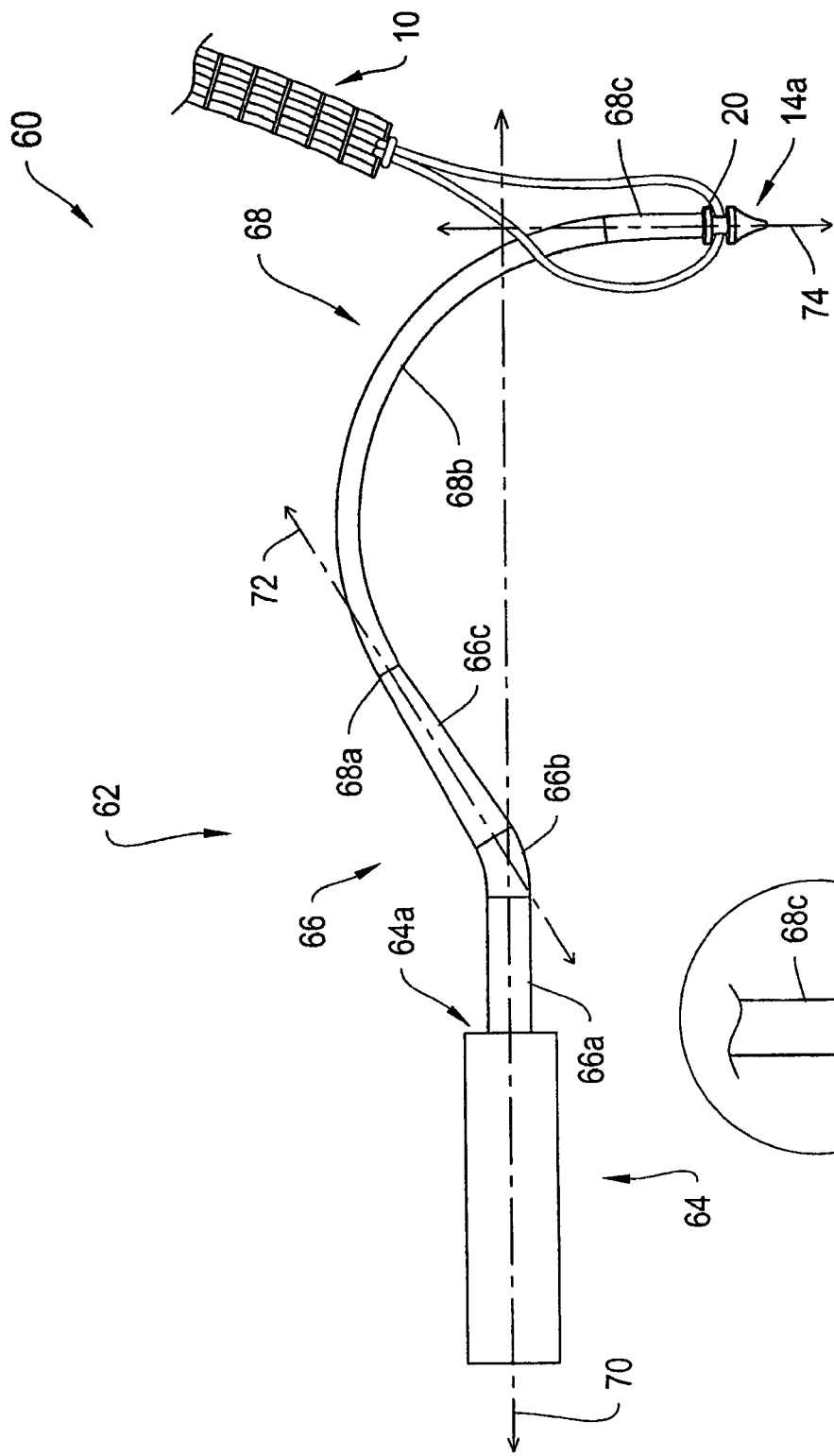
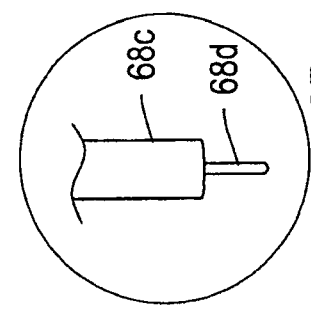
Figure 8A
Figure 8B

ELASTIC SLING SYSTEM AND RELATED METHODS

CROSS-REFERENCE TO RELATED APPLICATIONS

This application is a continuation of U.S. patent application Ser. No. 11/429,764, filed on May 8, 2006, claims the benefit of U.S. Provisional Application Nos. 60/702,539 and 60/702,540, both filed on Jul. 25, 2005, and U.S. Provisional Application No. 60/715,362, filed on Sep. 8, 2005, the contents of which are incorporated by reference herein in their entirety.

FIELD OF THE INVENTION

The invention generally relates to systems and methods for delivering a supportive sling to an anatomical location in a patient. More particularly, in various embodiments, the invention is directed to systems and methods relating to a sling assembly having an adjustable tensioning feature.

BACKGROUND

Pelvic floor disorders afflict many women. According to some studies, about 1 out of 11 women needs surgery for a pelvic floor disorder during her lifetime. The pelvic floor generally includes muscles, ligaments, and tissues that collectively act to support anatomical structures of the pelvic region, including the uterus, the rectum, the bladder, and the vagina. Pelvic floor disorders include vaginal prolapse, vaginal hernia, cystocele, rectocele, and enterocele. Such disorders are characterized in that the muscles, ligaments and/or tissues are damaged, stretched, or otherwise weakened, which causes the pelvic anatomical structures to fall or shift and protrude into each other or other anatomical structures.

Moreover, pelvic floor disorders often cause or exacerbate female urinary incontinence (UI). Urinary incontinence affects over 13 million men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). As a result, the patient's response time becomes insufficient to promote urethral closure and, consequently, the patient suffers from urine leakage and/or flow.

UI and pelvic floor disorders, which are usually accompanied by significant pain and discomfort, are typically treated by implanting a supportive sling in or near the pelvic floor region to support the fallen or shifted anatomical structures or to, more generally, strengthen the pelvic region by, for example, promoting tissue ingrowth. A popular treatment of SUI and uses a sling placed under the bladder neck or mid-urethra to provide a urethral platform. Placement of the sling limits the endopelvic fascia drop, while providing compression to the urethral sphincter to improve coaptation. Generally, the sling is placed close to the high-pressure zone with no elevation of the urethra. When abdominal pressure increases, the sling stops the descent of the urethra and functions as a mechanism for closing the urethra to prevent urine leakage.

However, if too much tension is applied, the patient may go into urine retention, unable to void the bladder. This results in a pressure build-up in the bladder, which can lead to reflux of urine up the ureters and into the kidneys, eventually resulting in kidney damage, and, potentially, kidney loss. Alternatively, if too little tension is applied, the implanted sling may not perform its function as intended.

Clinically, in vaginal incision techniques, it is challenging to both optimally position the slings and optimally adjust the tension of the sling during implantation while working through a relatively small single vaginal incision. It is sometimes necessary to modify the sling tension after the initial implantation, especially if the patient's anatomy has changed, for example due to weight gain. It would also be desirable to provide improved methods for adjusting sling tension to compensate for tension changes in the sling over time. Therefore, improved surgically implantable slings, and methods to allow for adjustment of the sling tension are needed.

SUMMARY

The systems and methods described herein are generally directed to the treatment of stress urinary incontinence. More particularly, in various embodiments, the invention Provides systems and methods relating to delivering a supportive sling to the periurethral tissue of a patient, without the need for abdominal or ischiopubic incisions. The sling may be sized and shaped for urethral and/or bladderneck support. The sling may be sized and shaped for supporting one or more pelvic floor organs. In certain implementations, the sling is delivered through a single vaginal incision. The single incision procedure can include placement of the sling via the vagina towards the transobturator, retro-pubic, pre-pubic or in a direction from the vagina towards another part of the human body. It is also understood that the invention is not limited to single incision procedures, and may be adapted to other pelvic floor and incontinence procedures. In one aspect, the invention makes it easier for a medical operator to accurately place the supportive sling at a desired anatomical location. In further embodiments, the invention makes it easier for a medical operator to dissociate a sling from a delivery device and/or a remaining portion of a sling assembly. According to additional embodiments, the invention provides for automatic adjustment of a sling member.

In one aspect, the invention provides a sling assembly, including a sling, first and second dilators, and at least a first elastic tensioning member, attached to the sling and dilators. The sling includes first and second ends and first and second longitudinal edges extending between the first and second ends. The first and second dilators each include proximal and distal ends, a passage extending axially at least part-way from the proximal end to the distal end, and optionally, a radial through-aperture located between the proximal and distal ends. In some embodiments, the axially extending passage extends all the way between the proximal and distal ends to form a through passage. Preferably, the radially extending through passage is sized and shaped to pass the first elastic tensioning member, and the axially extending passage is sized and shaped for interfitting over a distal end of a sling delivery device shaft.

In various embodiments, the first elastic tensioning member has first and second ends, the first end passing through the radially extending passage in the first dilator, and the second end attaching to the first end of the sling. Attachment to the sling may be, for example, by way of looping through one or more apertures in the sling end, or by knotting, clipping, gluing, stitching, or other suitable attachment mechanism.

The apertures in the sling may be particularly formed or may be naturally occurring interstitial spaces between the sling filaments. In some embodiments, the second dilator attaches directly to the second sling end, for example, by way of threading one or more sling filaments through the radially extending through aperture, or by gluing, heat bonding, shrink tubing, stitching or other suitable mechanism. However, in other embodiments, the sling assembly includes a second elastic tensioning member for attaching the second dilator to the second sling end. The elastic tensioning members may be formed from any suitable elastic, resilient material, such as, an elastic polymer material. According to one feature, the spring constant k of the elastic tensioning members is such that the elastic tensioning members exert 1.5 lb to 2.5 lb of force in the stretched state.

According to another embodiment, the sling assembly employs a single elastic tensioning member, which extends from the first dilator axially through the sling to the second dilator. In some embodiments, the tensioning member is a strand of elastic material, which interweaves through the sling from the first sling end to the second sling end, and attaches to the first and second dilators by way of knotting, gluing or other suitable mechanism.

In an alternative embodiment, the single elastic tensioning member is formed as an elastic loop, which threads through the radially extending aperture in the first dilator at a first end of the sling assembly, interweaves through the sling mesh from the first sling end to the second sling end, and threads through the radially extending aperture in the second dilator at a second sling assembly end. In a further configuration, two segments of the loop couple together and thread through the sling along a single path between the first and second sling ends. According to one feature, the two segments are attached, for example, by gluing, heat bonding, clipping, twisting, shrink tubing or other suitable mechanism.

According to some embodiments, the elastic tensioning member is elongatable. In one embodiment, after the elastic tensioning member has been elongated, it retracts to its original length, or to a shorter length, upon release of pressure. In another embodiment, after the elastic tensioning member has been elongated, it remains elongated, and does not retract to a shorter length.

According to various embodiments, the first and second dilators may have any of a plurality of configurations. According to one embodiment, the dilators expand in diameter along at least a portion of their length as they extend from their respective distal to proximal ends. According to one feature, the degree of diametric expansion is large enough to dilate the patient's tissue sufficiently to ease passage of the remainder of the sling assembly.

In some embodiments, the dilators also act as a soft tissue anchor. In such embodiments, the dilators may include one or more radially extending projections, edges, tapers, shoulders, barbs or other protrusions sized and shaped for facilitating passage of the dilators into the patient's tissue, and for resisting removal of the dilators subsequent to sling assembly implantation. In one configuration, the dilators include a reduced diameter section, which forms a shoulder in the body of the dilator. According to one feature of this embodiment, the shoulder is located proximal to the conical tip and engages with the patient's tissue to resist removal of the dilator subsequent to the sling assembly be implanted.

According to one embodiment, the sling of the sling assembly includes a first plurality of filaments located between the first and second longitudinal edges and extending between the first and second sling ends. In one configuration, the filaments are oriented substantially parallel to each other.

According to a further configuration, the sling includes a second plurality of filaments extending laterally across the first plurality of filaments from the first longitudinal edge to the second longitudinal edge. According to one feature, the first plurality of filaments are located about perpendicular to the second plurality of filaments. According to one configuration, at least some of the sling filaments are formed from a single stranded material. According to another configuration, at least some of the sling filaments are formed from a multi-stranded material.

According to one configuration, the sling or sling assembly includes features for indicating length measurements for aiding in positioning of the sling. According to one configuration, the sling and/or sling assembly also includes a feature for indicating a center location along the length of the sling, also for aiding in accurate sling placement. Preferably, the center feature, and the length measurement and/or position-indicating features are distinguishable from each other. By way of example, the length measurement and/or position-indicating features, and center features may be differently colored and/or of different widths.

In a further aspect, the invention provides a system for delivering a sling to an anatomical location in the body of a patient. More particularly, in various embodiments, the invention provides a system for delivering a sling assembly to the periurethral tissues of a patient to provide a urethral platform for treating urinary incontinence. According to one embodiment, the system of the invention includes a sling assembly of the type described above and a delivery device.

The delivery device may be particularly configured for any delivery approach, including, without limitation, a transvaginal, abdominal, or transobtural approach. For example, in one configuration, the delivery device includes a handle, a shaft, and a pusher assembly slidably interfitted over the shaft. The pusher assembly includes an actuator located near the distal end of the handle, and a cannula extending distally from the actuator along the shaft. The dilator of a sling assembly, for example, of the type described above, can be interfitted over the distal end of the shaft and slid proximally along the shaft to abut a shoulder created by a distal end of the pusher assembly cannula. The handle, shaft, and pusher assembly may include any combination of curved and straight sections, and may extend in one, two or three dimensions.

In operation, a medical operator may use the actuator to slide the pusher assembly distally along the shaft, causing the shoulder at the distal end of the pusher assembly cannula to engage with a proximal end of the dilator and push the dilator off the delivery device shaft. This may occur, for example, following implantation of the dilator into the periurethral tissue of a patient.

According to another embodiment, the delivery device includes a handle with first and second substantially straight sections located substantially in a first plane and angled relative to each other, a transitional portion extending out of a distal end of the handle, and a shaft extending from a distal end of the transitional portion. The shaft includes a curved section and a straight section, and terminates in a conical tip.

The transitional portion interfits and extends axially out of the distal end of the second handle section to affix the shaft to the handle. As a result, the transitional portion is substantially co-planar with the handle in the first plane. The curved section of the shaft extends from a distal end of the transitional portion. The straight section of the shaft extends from a distal end of the curved section. The curved section and the straight section are substantially coplanar in a second plane. According to one configuration, the first and second planes are substantially orthogonal to each other. However, the first and second planes may be at any suitable angle (e.g., about 10, 20, 30, 45, 60, 70 or 80 degrees) to each other. In another embodiment, the first and second sections of the handle are at an angle of about 150 degrees to each other. However, the first and second sections of the handle may be at any suitable angle (e.g., about 80, 90, 100, 110, 120, 130, 140, 160, 170 or 180 degrees) to each other.

To provide structural reinforcement, the first and second handle sections have a cross sectional diameter that tapers to be smaller at the distal end of the handle. Additionally, the transitional portion may be formed as part of the handle, part of the shaft or independently from the handle and the shaft.

According to a further embodiment, the delivery device includes a handle, a shaft, and a transitional portion extending distally between a distal end of the handle and a proximal end of the shaft, with the handle, transitional portion and shaft all substantially coplanar. In one configuration, the transitional portion includes a first straight section, a curved section and a second straight section, and may be formed as either part of the shaft or as part of the handle. According to a further configuration, the shaft includes a curved section, a straight section and a conical tip. The first straight section of the transitional portion attaches to the distal end of the handle, extends distally along a first axis, and preferably, has a substantially constant diameter. The curved section of the transitional portion extends from a distal end of the first straight section, curves away from the first axis, and also preferably, has a substantially constant diameter. The second straight section of the transitional portion extends from a distal end of the curved section along a second axis, and preferably, has a diameter that decreases from its proximal end to its distal end to provide increased structural stability to the shaft. The curved section of the shaft, preferably, has a substantially constant diameter, smaller than the diameter of the curved section of the transitional portion, and extends from the distal end of the second straight section of the transitional portion, curves back toward the first axis, and terminates at a distal end approximately at an intersection with the first axis. The straight section of the shaft, preferably, has a substantially constant diameter and extends from the distal end of the curved section of the shaft along a third axis, which crosses the first axis. A conical tip extends distally from the straight section of the shaft.

According to a further aspect, the invention provides various methods for delivering an implant, such as a sling or sling assembly, to an anatomical site in the body of a patient. The methods include, without limitation, trans-obturatural, suprapubic, prepubic, and transvaginal approaches.

According to one method, the sling assembly is delivered transobturally using a delivery device, such as those described above. To begin, an incision is made in the anterior vaginal wall and dissected bilaterally to the interior portion of the inferior pubic ramus. The dilator of a sling assembly, for example, of the type described above, attached to an end of the sling is interfitted over the distal end of the delivery device shaft. A medical operator grasps the handle and inserts the delivery device shaft portion with the dilator installed through the vaginal incision. With a lateral motion, the medical operator passes the curved portion of the delivery device shaft behind the ischiopubic ramus and pierces the obturator membrane. The operator then elongates an elastic member of the sling assembly, and the elastic member is inserted through a hole in the obturator membrane. The operator may elect to guide the device to a location beneath the patient's epidermis to secure the implant in the patient's soft tissue. The delivery device shaft can then be withdrawn from the body leaving the dilator implanted in or through the obturator membrane, and optionally, fixed to the obturator membrane. No other incisions are needed for implantation of the dilator (although additional groin, gluteal, or other incisions may be used if desired). This process is repeated with the same or a second delivery device having an opposite curvature and the second dilator, through the same incision, to implant the second dilator in or through the obturator membrane on the contralateral side of the body. The sling forms a supportive platform under the urethra.

According to another method, the dilators of the sling assembly are positioned at any suitable location in the periurethral tissues of the body of the patient. In one such approach, a pusher assembly on the delivery device is actuated to push each dilator off of the delivery device when the respective dilator is suitably positioned. In some embodiments a single delivery device is employed, while in other embodiments, two delivery devices are employed.

Other aspects and advantages of the invention are described below with respect to various illustrative embodiments.

BRIEF DESCRIPTION OF THE DRAWINGS

The following figures depict certain illustrative embodiments of the invention in which like reference numerals refer to like elements. These depicted embodiments may not be drawn to scale and are to be understood as illustrative of the invention and not as limiting in any way.

FIGS. 8A and 8B show a delivery system including a delivery device having a handle and a shaft, the shaft having a curved section located substantially coplanar with the handle, and a sling assembly having a dilator/anchor interfitted over a distal end of the delivery device shaft according to an illustrative embodiment of the invention.

ILLUSTRATIVE DESCRIPTION

As described above in summary, the invention addresses deficiencies in the prior art by, in various illustrative embodiments, providing improved systems, methods and devices relating to implanting supportive slings within the human body. In particular illustrative embodiments, the systems, methods and devices of the invention are sized, shaped and adapted for delivering a sling to periurethral tissue to provide urethral, bladder, and/or bladder neck support for treating urinary incontinence.

As described below in further detail, some of the illustrative embodiments are directed to improved slings and sling assemblies. Other illustrative embodiments are directed to improved tissue anchors, such as soft tissue anchors, for anchoring one or both ends of a sling or sling assembly at a desired anatomical location. Further illustrative embodiments, are directed to anchor sized dilators, which in various implementations may be sized and shaped like any of the described anchors, except with substantially smooth outer surfaces. In some of these illustrative embodiments, the dilator/anchor relies on dilator/anchor orientation, rather than barbs for anchoring.

In some illustrative embodiments, the improved anchors/dilators include, for example, improved anchoring structures, improved interfittings with delivery devices, and improved features for automatically tensioning the sling assembly. Additional illustrative embodiments are directed to improved delivery devices and sling delivery systems. The illustrative delivery systems include, for example, a sling assembly along with a delivery device. Other illustrative embodiments describe exemplary procedures for implanting a supportive sling employing features of the invention.

According to one advantage, the sling assemblies provide for an automatically adjustable sling for tensioning the support of the periurethral tissue of a patient. According to another advantage, the sling assemblies facilitate delivery of the supportive sling to the periurethral tissue of a patient, without the need for abdominal or ischiopubic incisions. According to other advantages, the invention makes it easier for a medical operator to accurately place the supportive sling at a desired anatomical location. According to further advantages, the elastic member eliminates or mitigates the need for a medical operator to adjust the effective length of a sling.

Figures 1A, 1B:
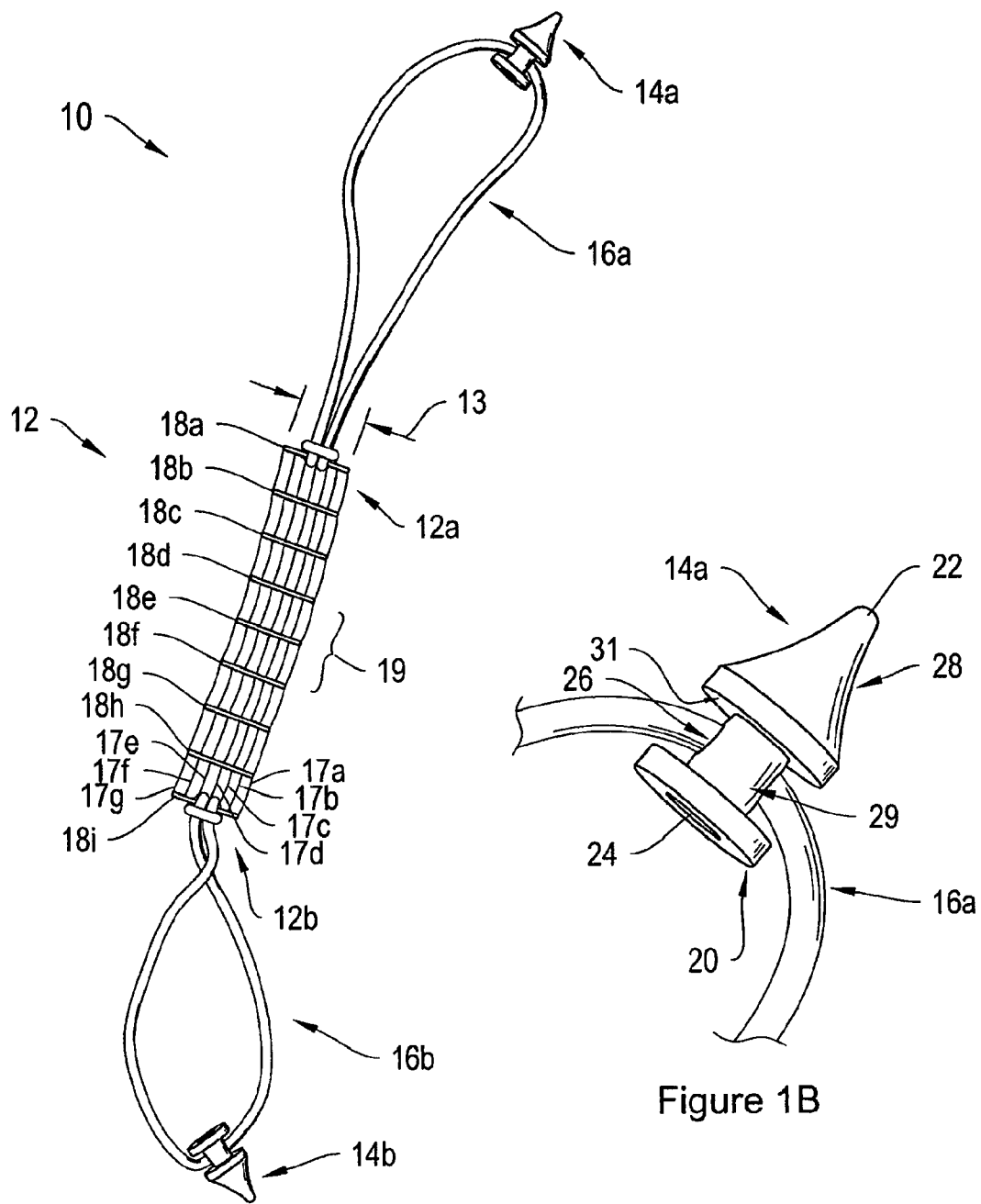
FIG. 1A is a top view of a sling assembly including a sling, elastic members, and tissue anchor/dilators, according to an illustrative embodiment of the invention.
FIG. 1B is an enlarged, perspective view of a tissue anchor/dilator for affixing a sling end at an anatomical site according to an illustrative embodiment of the invention.

Turning to the depicted illustrative embodiments, FIGS. 1A and 1B depict top and enlarged views, respectively, of a sling assembly 10 according to an illustrative embodiment of the invention. The sling assembly 10 includes a mesh sling 12, first 14a and second 14b dilator/anchors, and first 16a and second 16b elastic members. According to the illustrative embodiment of FIG. 1A, the sling assembly 10 has an end-to-end length measured from the distal tips 22 of the anchor/dilators 14a and 14b of between about 10 cm and about 17 cm in an unstretched state.

The sling 12 has first 12a and second 12b ends, a plurality of filaments 17a-17g (generally "longitudinal elements 17") extending longitudinally between the first 12a and second 12b ends, and a plurality of filaments 18a-18i (generally "laterally extending filaments 18") spaced apart along a length of the sling 12 and extending laterally across the filaments 17a-17g at about a 90° angle to the filaments 17a-17g. While FIG. 1A depicts a sling 12 having seven longitudinal filaments 17 and nine laterally extending filaments 18, in alternative implementations, the sling 12 may have any fewer or more longitudinal filaments 17 and laterally extending filaments 18. The sling 12 may also employ any suitable configuration. However, one advantage of the sling 12 is that it is less stretchable than a sling employing a conventional cross-hatched mesh configuration. According to the illustrative embodiment, in a substantially unstretched state, the sling 12 is about 5 cm to about 7 cm long. However, any suitable sling length may be employed.

In an illustrative use, a middle section 19 of the sling 12 is located beneath an anatomical site, such as a midurethral or bladder neck location in the periurethral tissue. In one illustrative embodiment, the middle section 19 of the sling 12 has smooth or rounded edges, hereinafter also referred to as "non-tanged" edges. According to a further illustrative embodiment, other sections of the sling 12 may include tangs (e.g., sharp projections or frayed edges). The tangs are useful for anchoring the sling 12 and encouraging tissue growth into the sling 12.

Tanged and non-tanged edges of the mesh sling 12 may be formed in a plurality of ways. For example, the sling 12 can be cut from a woven sheet, in which case the edges may be initially tanged along an entire length of the sling 12. One or more non-tanged sections may be formed by any process that smoothes, rounds or removes the sharp edges of the tangs. For example, the tangs may be heat-smoothed by burning or melting the tangs. Providing one or more non-tanged sections, which may be in close proximity to a sensitive anatomical site in the patient, can enhance the comfort level of the patient and reduce the potential for the edges of the tangs to erode or irritate the urethra. Alternatively, the sling 12 can be produced from a woven tape having the approximate finished width of the sling 12. The smooth sides of the tape can then be trimmed off to produce the tanged sections.

Figure 10:
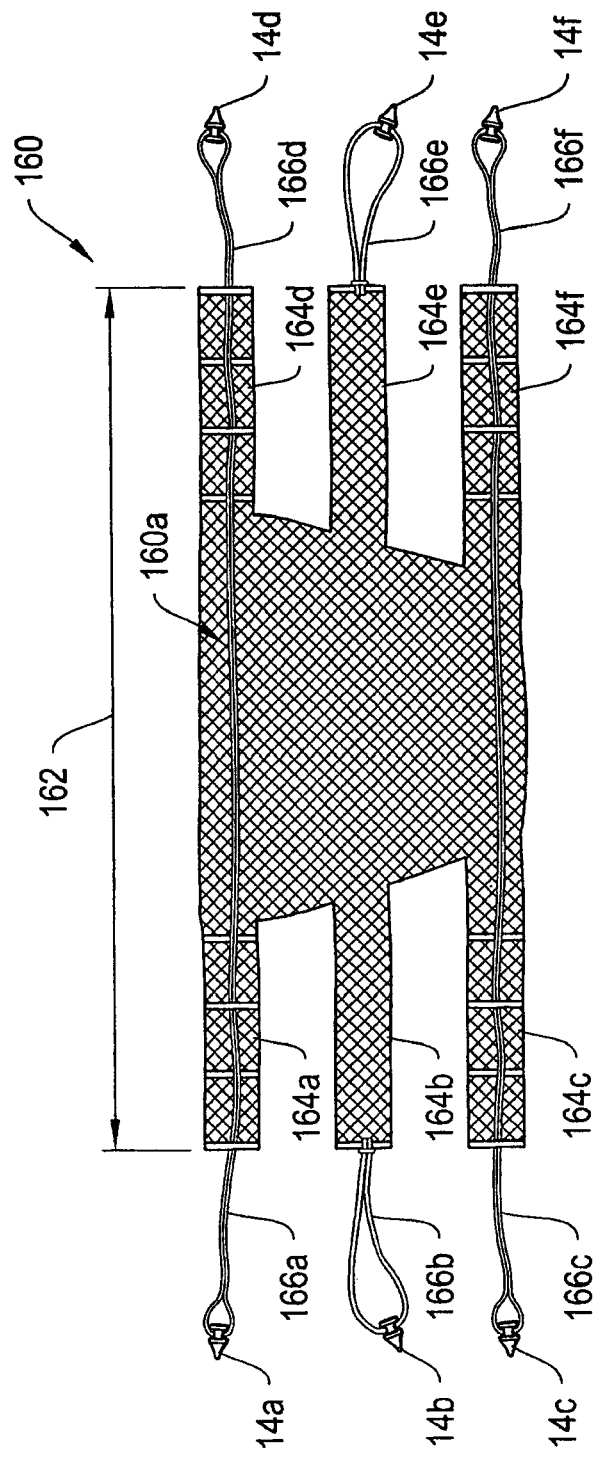
FIG. 10 shows a pelvic floor implant having a central region and six elastic members and anchor/dilators, according to an illustrative embodiment of the invention.

According to various embodiments, the sling assembly 10 may be configured as an implant that is sized and shaped to support one or more organs in the patient's pelvic floor. As shown in FIG. 10, and discussed in greater detail below, a pelvic floor implant may include a central portion and a plurality of elastic members.

The sling 12 used with the invention may be fabricated from any suitable material(s), preferably biocompatible materials. In certain illustrative embodiments, the material may include, for example, synthetic mesh or other synthetic material; it may also or alternatively include non-synthetic material, such as cadaver, human or animal tissue; it may also include any combinations thereof. In examples employing synthetic material for the sling 12, it may be derived from any suitable synthetic material. Such material could include, for example, polymeric material such as, for example, Polytetrafluorethylene (Goretex), polypropylene (Marlex), polyethylene (Mersiline), silastic, or impregnated collagen matrix (Protegen).

Other suitable synthetic materials for the sling 12 may include, for example, nylon, polyethylene, polyester, polypropylene, fluoropolymers, copolymers thereof, combinations thereof, or other suitable synthetic material(s). The material may be a synthetic material that is absorbable by the patient's body. Suitable absorbable synthetic materials can include polyglycolic acid, polylactic acid, and other suitable absorbable synthetic materials. The filament mesh sling 12 material may be fabricated from one or more yarns, which yarns may be made from one or more materials.

Alternatively, the materials for the sling 12 may employ non-synthetic or natural materials, for example materials from human fascia, cadaveric fascia, or other mammalian tissue(s). Human tissues may be used in certain embodiments and may be derived, for example, from human cadaveric or engineered human tissue. Animal tissues may be derived, for example, from porcine, ovine, bovine, and equine tissue sources. In certain embodiments the materials for the sling 12 may include a combination of non-synthetic (e.g., mammalian tissue(s)) and synthetic materials.

According to a further illustrative embodiment, any or all of the sling 12 may be configured to be biodegradable/bioabsorbable. According to another feature, at least a portion of the sling 12 is biodegradable and may also dissolve and/or be absorbed into the patient's tissues. For example, in some embodiments, only a section of the sling 12 is biodegradable/bioabsorbable, such as, for example, an intermediate portion. Examples of biodegradable/bioabsorbable materials that may be used for the sling 12 include, without limitation, polylactic acid (PLA), polyglycolic acid (PGA), poly-L-lactic acid (PLLA), human dermis and decellularized animal tissue.

Exemplary biodegradable/bioabsorbable materials, in addition to those listed above, which may be employed for the sling 12 include, but are not limited to, polylactic acid, polyglycolic acid and copolymers and mixtures thereof, such as poly(L-lactide) (PLLA), poly(D,L-lactide)(PLA), polyglycolic acid [polyglycolide (PGA)], poly(L-lactide-co-D,L¬lactide) (PLLA/PLA), poly(L-lactide-co-glycolide) (PLLA/PGA), poly(D,L-lactide-co¬glycolide) (PLA/PGA), poly(glycolide-co-trimethylene carbonate) (PGA/PTMC), poly(D,L¬lactide-co-caprolactone)(PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, polyphosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as gelatin and collagen; and mixtures and copolymers thereof.

According to a further illustrative embodiment, the sling 12 may incorporate, be coated or otherwise treated with one or more agents for providing a therapeutic effect, for example, to reduce discomfort, to reduce the chance of infection and/or to promote tissue growth. In some embodiments, the agent may be configured to release into the patient's tissues.

One illustrative agent promotes, when applied to the patient's tissues in a pharmaceutically acceptable amount, well-organized collagenous tissue growth, such as scar tissue growth, preferably in large quantities. The tissue growth factor may include natural and/or recombinant proteins for stimulating a tissue response so that collagenous tissue growth, such as scar tissue growth, is enhanced. Exemplary growth factors that may be used include, but are not limited to, platelet-derived growth factor (PDGF), fibroblast growth factor (FGF), transforming growth factor-beta (TGF-beta), vascular endothelium growth factor (VEGF), activin/TGF and sex steroid, bone marrow growth factor, growth hormone, insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues.

According to other illustrative embodiments, the therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, alclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen-, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as E-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof. Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papavereturn, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocalne hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocalne, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammoniwn bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n-trimethyl-3,3-diphenyl-propylamine, tropenzile, trospium chloride, xenytropium bromide, and pharmaceutically acceptable salts thereof.

The agent(s) may be associated with the sling 12 in a variety of manners. For example, the agent may be chemically or physically attached to the surface of the sling 12. In one illustrative embodiment, one or more surfaces of the sling 12 and the agent, for example, in solution, have complementary ionic charges. As such, when placed on the sling 12, the agent ionically bonds to the one or more surfaces.

According to another illustrative embodiment, the sling 12 may incorporate a protective treatment/coating, which is preferably biocompatible and may be bioabsorbable/dissolvable. Such protective treatments include, but are not limited to, alginates, sugar based formulations, starches, gelatins, cellulose, polyvinyl alcohol, polyglycolic acid (PGA), polylactic acid (PLA), polydioxinone (PDO), and/or other synthetic or natural polymers including combinations thereof. The treatment materials may cover any portion or all of the sling 12. In one particular configuration, the protective treatment encapsulates or substantially encapsulates at least a portion of the sling 12. According to one feature, the protective treatment is formed from lubricious material, which reduces the friction between the sling 12 and the patient's periurethral tissues. In this way, the protective treatment can provide a relatively smooth tissue contact surface to otherwise tanged or ragged sling edges to reduce the likelihood of the filament mesh sling 12 irritating the patient's tissues during implantation.

The protective treatment may be applied to the sling 12 by any suitable approach, for example, by way of spraying, brushing or dipping the portion of the sling 12 to be treated. According to another illustrative embodiment, the protective treatment is formed as a sheet of material that can be affixed to the portion of the sling 12 to be treated. According to another feature, the protective treatment may be configured to dissolve within a particular time range. The protective treatment may be configured, for example, to substantially absorb into the patient's tissues within about 5, 10, 15 or 30 minutes from the time the sling 12 is implanted. Alternatively, the protective treatment may be configured to substantially absorb into the patient's tissues over a time span of hours, days, weeks, or months.

In another illustrative embodiment, before application of the agent, the protective treatment is applied to the sling 12. According to another illustrative embodiment, the protective treatment and the agent are mixed to form a single treatment and then applied to the sling 12 in a one step process.

According to the illustrative embodiment of FIGS. 1A and 1B, the anchor/dilators 14a and 14b are substantially identical. As shown most clearly in the enlarged view of FIG. 1B, the tissue anchor/dilator 14a includes a proximal end 20 and a distal tip 22. A channel 24 sized and shaped for interfitting over a distal end of a delivery device shaft extends axially at least part way between the proximal end 20 and distal tip 22. The anchor/dilator 14a also includes a radially extending aperture 26 sized and shaped for slidably interfitting with the elastic member 16a. The anchor/dilator tip 22 may have any suitable shape, including being sharpened to pierce tissue or being rounded blunt. The anchor/dilator tip 22, preferably, is sufficiently sharp such that when axial force is applied, the anchor/dilator tip 22 penetrates tissue, such as an orbital membrane.

As shown, dilator/anchor 14a includes a conically shaped portion 28, which tapers outward with its diameter increasing as it extends from the distal tip 22 at least part way to the proximal end 20. The conically shaped portion 28 dilates the patient's tissue to better accommodate the width 13 of the sling 12 during implantation. In some illustrative configurations, the conically shaped portion 28 extends all the way from the distal tip 22 to the proximal end 20. As shown in FIGS. 1A and 1B, according to the illustrative embodiment, the dilator/anchor 14a includes a reduced diameter section 29 located between the distal tip 22 and proximal 20 ends. The reduced diameter section 29 creates a shoulder 31 that can engage with the patient's tissues and resist removal of the anchor/dilator 14a subsequent to implantation. In other illustrative embodiments, the anchor/dilator 14a includes one or more radially extending barbs or other projections for resisting removal. The tissue anchors/dilators 14a and 14b of the invention may also have relatively smooth outer surfaces, and rely on orientation for resisting removal from a patient's tissue once implanted.

According to some configurations, the illustrative anchors/dilators 14a and 14b have an outside diameter of between about 6 mm and about 10 mm. In further illustrative configurations, the anchor/dilators 14a and 14b are between about 0.5 cm and about 2 cm long. According to other illustrative configurations, the anchors/dilators 14a and 14b are composed, at least in part, of a polymer material. However, any suitable material may be used, such as those enumerated above.

As is the case with any of the anchors/dilators described herein, the tissue anchor/dilator 14a may be inserted into any suitable soft tissue in a patient, including ligaments, muscles, cartilage, fibro-fatty tissue, organs, and soft portions of bones or bone coatings. As is also the case with any of the tissue anchors/dilators of the invention, the tissue anchors/dilators 14a-14b may be formed from any suitable biocompatible material, such as any suitable polymer material. As described below in more detail, the anchors/dilators may also be coated or otherwise treated with any suitable material.

In certain illustrative embodiments, any of the materials described above for use with the sling 12 may also be used for any of the anchors/dilators of the invention. For example, any or all of the anchors/dilators may be configured from synthetic materials, non-synthetic materials, or both. Moreover, the anchors/dilators may be prepared to include a protective coating or treatment, as described above in reference to the sling 12. They may also be configured to contain an agent for release into the patient's tissues, as described above in reference to the sling 12. Any such configurations may adopt any of the materials suitable for the sling 12 for use with the anchors/dilators of the invention.

According to the illustrative embodiment of FIGS. 1A and 1B, the elastic members 16a and 16b are each formed from a single filament configured as a unitary loop. The elastic members 16a and 16b are made from a stretchable silicon based material. However, they may be made from any suitably stretchable material, including rubber, a low density polyethylene, or a suitable deformable plastic. The elastic member 16a threads through the aperture 26 in the anchor/dilator 14a and attaches to the sling end 12a, for example, by looping, tying, suturing, gluing, stapling or any other suitable mechanism. In the particular illustrative embodiment of FIGS. 1A and 1B, the elastic member 16a loops around the laterally extending filament 18a to attach the elastic member 16a to the sling end 12a. Similarly, the elastic member 16b threads through a corresponding aperture in the dilator/anchor 14b and attaches to the sling end 12b in the same fashion.

In an unstretched state, according to some illustrative embodiments, the elastic members 16a and 16b are between about 2 cm and about 5 cm in length. In other illustrative embodiments, the elastic members are between about 2.3 cm and about 3.5 cm in length. According to some illustrative embodiments, the elastic members 16a and 16b extend an additional amount of between about 1 cm and about 3 cm in a stretched state, or in some illustrative embodiments an additional amount of between about 1.5 cm and about 2 cm. According to a further illustrative embodiment, the spring constant k of each of the elastic members 16a and 16b is such that they each exert a force of between about 1.5 lb to about 2.5 lb in the stretched state. The spring constant k of each of the elastic members 16a and 16b may be such that they each exert a force of less than about three (3) lbs in the stretched state.

According to one embodiment, the elastic members 16a and 16b are made of material that allows the stretchability to vary. In certain embodiments, a silicon rubber material is used which allows the members 16a and 16b to stretch and return to their original unstretched length after stretching. According to an alternative embodiment, the elastic members 16a and 16b are made of a thin polymer film or a polymer that has been cross-linked, which allows the members 16a and 16b to stretch but, after stretching the elastic members 16a and 16b, the elastic members 16a and 16b remain in an elongated state at their stretched length. Other suitable irreversibly stretchable materials that may be used include low density polyethylene and suitable deformable plastics, e.g. ductal polymers. In one embodiment, the elongation force necessary to stretch elastic members 16a and 16b is set at least about 3 lbs, and the spring constant k of each elastic member 16a and 16b is such that they each exert a force of less than about 3 lbs.

Figure 2:
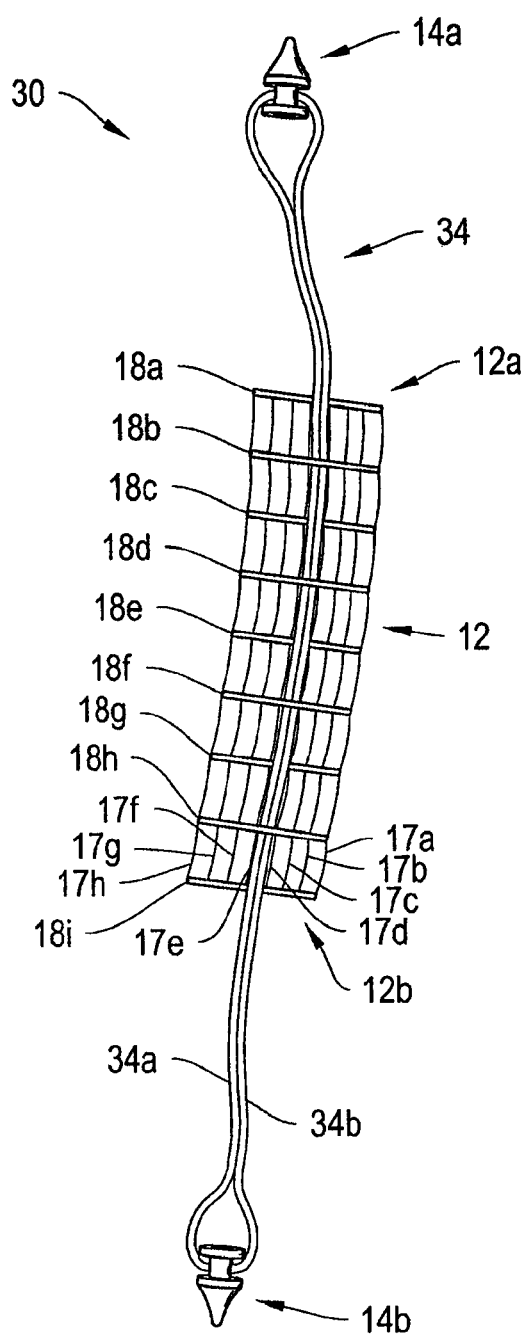
FIG. 2 is a top view of a sling assembly including a sling, a single elastic member coupled to the sling via interweaving thereof, and anchor/dilators, according to an alternate illustrative embodiment of the invention.

FIG. 2 shows a sling assembly 30 according to an alternative illustrative embodiment of the invention. The sling assembly 30 includes a sling 12, a single elastic member 34, and anchors/dilators 14a and 14b. The sling 12 and the anchor dilators 14a and 14b of FIG. 2 are of the same type as described above with respect to FIGS. 1A and 1B, though sling 12 in FIG. 2 includes one additional longitudinal filament 17h, not included in the sling 12 of FIGS. 1A and 1B. As in the case of the elastic members 16a and 16b of FIGS. 1A and 1B, the elastic member 34 is also formed from a single filament configured as a unitary loop. However, as described above with respect to the elastic members 16a and 16b, the elastic member 34 may be configured in any suitable fashion and formed from any suitably elastic material.

As shown in FIG. 2, the elastic member 34 extends axially through the sling 12 passing through both sling ends 12a and 12b, and through the radially extending aperture 26 of both anchor/dilators 14a and 14b. According to one feature, the elastic member 34 is interwoven through the sling 12, alternatively passing over and under the lateral filaments 18a-18i. However, in other illustrative embodiments, the elastic member 34 may be attached to the sling 12 using any suitable mechanism, including, for example, stitching, gluing, tying, suturing, or stapling. According to another feature, the elastic member 34 includes two axially extending segments 34a and 34b, which are located adjacent to and in contact with each other at least along the portion of the elastic member 34 that is interwoven with the sling 12. In a further illustrative embodiment, the axially extending segments 34a and 34b are attached together at least along the length of the sling 12. The two sides 34a and 34b of the elastic member 34 may also be attached together for a portion of their length extending axially from the sling end 12a toward the anchor/dilator 14a and from the sling end 12b toward the anchor/dilator 14b. The two segments 34a and 34b of the elastic member 34 may be attached together using any suitable method, including, for example, gluing, stitching, tying, heat bonding or suturing.

According to the illustrative embodiment, in an unstretched state, the elastic member 34 is between about 9 cm and about 13 cm in length. In other illustrative embodiments, in an unstretched state, the elastic member 34 is between about 5 cm and about 7 cm in length. According to the illustrative embodiment, the elastic member 34 extends an additional amount of about 3 cm to about 4 cm in a stretched state. According to a further illustrative embodiment, the spring constant k of the elastic member 34 is such that it exerts a force of between about 1.5 lb to about 2.5 lb in the stretched state. The spring constant k of the elastic member 34 may be such that it exerts a force of less than about 3 lbs. As in the illustrative sling assembly 10, the sling assembly 30 is between about 10 cm and about 17 cm long, measured between the distal tips 22 of the anchor/dilators 14a and 14b.

According to one embodiment, after stretching the elastic member 34, the elastic member 34 returns to its original unstretched length. According to an alternative embodiment, after stretching the elastic member 34, the elastic member 34 remains in an elongated state at its stretched length. In one embodiment, the elongation force necessary to stretch elastic member 34 is set at least about 3 lbs, and the spring constant k of the elastic member 34 is such that it each exerts a force of less than about 3 lbs.

Figure 3:
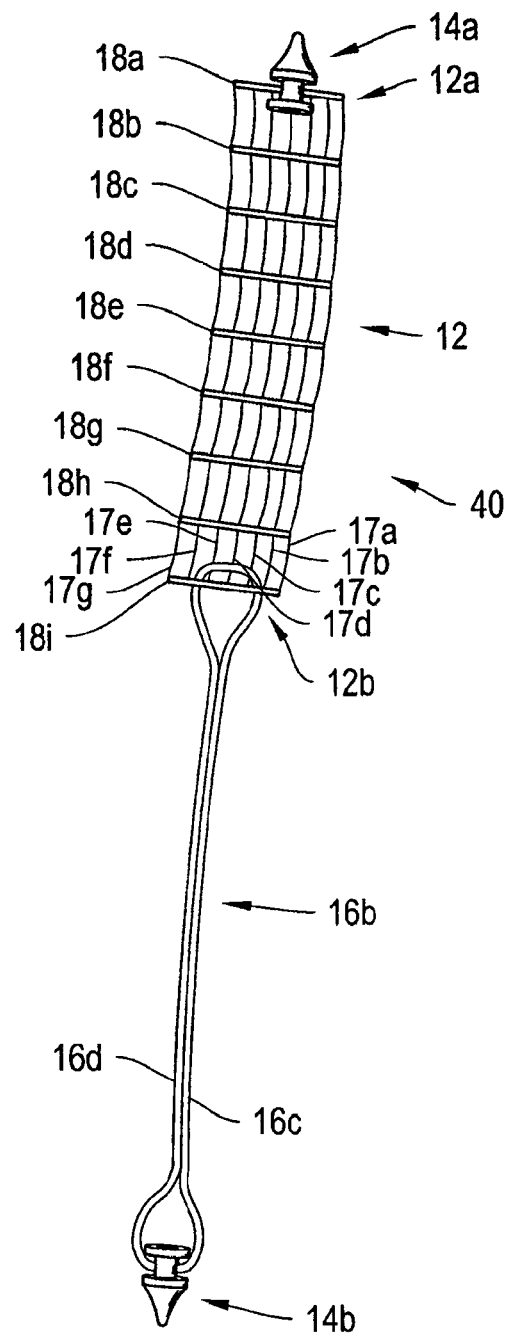
FIG. 3 is a top view of a sling assembly including a sling, a single elastic member looped through the sling, an anchor/dilator attached directly to the sling, and another anchor/dilator attached to the sling via the elastic member, according to another illustrative embodiment of the invention.

FIG. 3 shows a sling assembly 40 according to another illustrative embodiment of the invention. The sling assembly 40 includes a sling 12, an elastic member 16b, and anchors/dilators 14a and 14b. The sling 12 and the anchor dilators 14a and 14b of FIG. 3 are of the same type as described above with respect to FIGS. 1A-2. Additionally, the elastic member 16b is of the same type described above with respect to FIGS. 1A and 1B.

According to the illustrative embodiment of FIG. 3, the anchor/dilator 14a is attached directly to the end 12a of the sling 12. As shown, the lateral filament 18a at the end 12a of the sling 12 threads through the aperture 26 in the anchor/dilator 14a, attaching the anchor/dilator 14a to the sling 12. As also shown, the elastic member 16b threads through the radially extending aperture 26 in the anchor/dilator 14b and through the sling end 12b to attach the anchor/dilator 14b to the sling end 12b. Although the elastic member 16b is depicted as looping through apertures in the sling end 12b to attach the anchor/dilator 14b to the sling end 12b, the elastic member 16b may attach to the sling 12 using any suitable mechanism, as described above. According to another feature and in a similar fashion to the illustrative embodiment of FIG. 2, the elastic member 16b includes two axially extending segments 16c and 16d, which attach together for at least a portion of their length. The two segments 16c and 16d of the elastic member 16b may be attached together using any suitable method, including, for example, gluing, stitching, tying, heat bonding, or suturing. According to the illustrative embodiment of FIG. 3, the sling assembly 40 has a dilator tip-to-tip length of between about 8 cm and about 16 cm, with the sling 12, dilator/anchors 14a and 14b, and elastic member 16b being sized similarly sized to their counterparts described above with respect to FIGS. 1A and 1B.

According to various illustrative embodiments, the sling assemblies of the invention may be implanted into the body of a patient to support an anatomical site. In operation, the anchor dilators 14a and 14b are inserted into patient tissues one at a time to expand a tunnel through which at least a portion of the sling assembly travels. The dilators may be inserted with a suitable delivery device, or in some instances, with only the fingers of a medical operator. In particular illustrative embodiments, the sling assemblies of the invention are used to treat urinary incontinence, vaginal prolapse, or to provided pelvic floor reconstructive support. In some instances, the dilator/anchors 14a and 14b are inserted into the patient's tissues via an incision in the vaginal wall of the patient. According to some illustrative embodiments, the dilator/anchors 14a and 14b include structures, such as radial projections, for anchoring the sling assembly in place when implanted. In other illustrative embodiments, the dilator/anchors 14a and 14b do not provide any or only minimal tissue anchoring functionality.

In various approaches, the dilator/anchors 14a and 14b may be implanted into any suitable patient tissues, such as and without limitation, the tissue between the ischiocavernous pubic muscle and the ischiopubic bone; in front of the pubic bone; behind the pubic bone; in front of, embedded within, or through the obturator foramen; in the periurethal tissues; or in any suitable muscle, ligament or other tissue or anatomical structure within the abdomen. As mentioned above, according to one feature of the invention, one or more elastic members included in the sling assemblies of the invention allow the overall dilator/anchor tip-to-tip length of the sling assemblies to stretch and contract to automatically adjust the length to accommodate, for example, patient movement, muscle contractions, various patient positions, and change in anatomical size (e.g., gain or loss of weight or change in height) of the patient.

Figure 4:
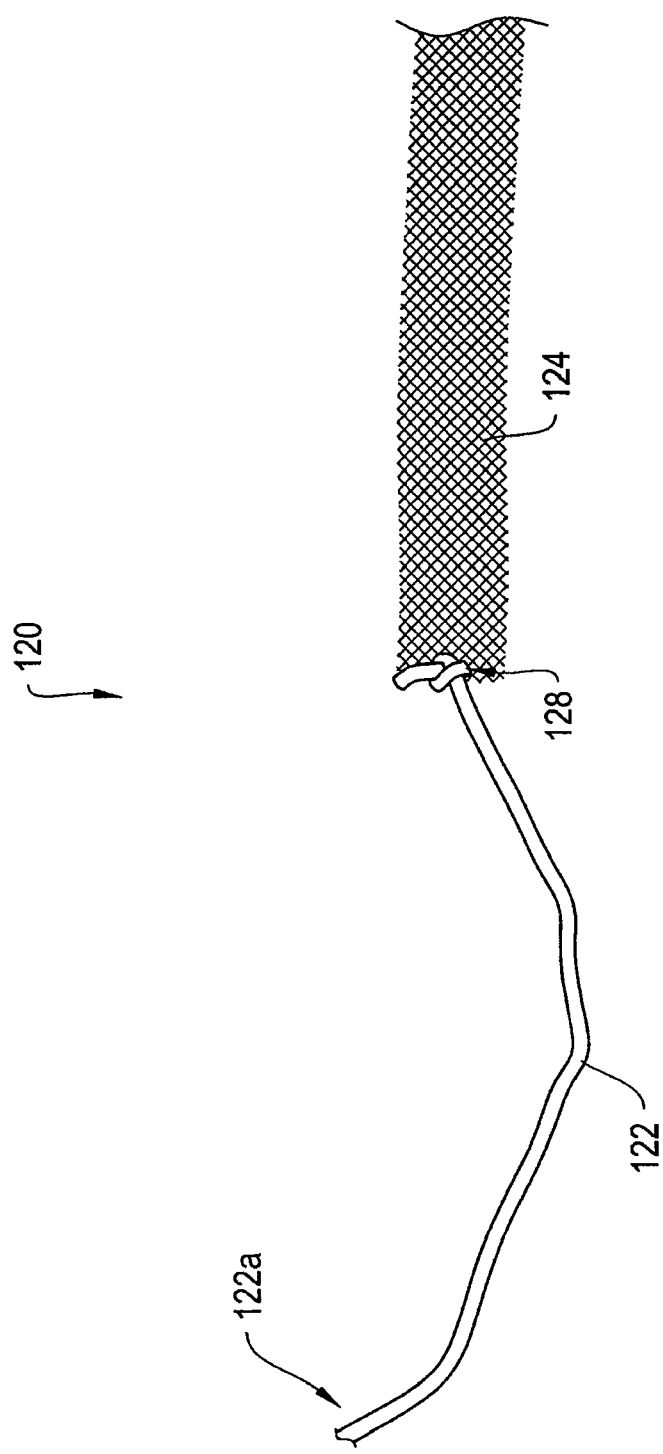
FIG. 4 is a top view of one end of a sling assembly, including an elastic member coupled to a sling, according to an illustrative embodiment of the invention.

FIG. 4 is a top view of one end of a sling assembly 120, including an elastic member 122 coupled to a mesh sling 124, according to an illustrative embodiment of the invention. The elastic member 122 is a single elastic strand, threaded through a hole in the mesh and attached to the sling 124 with a knot 128. The elastic member may be attached to the sling using any suitable method, including suturing, gluing, heat-sealing, and molding. In some embodiments, a dilator, such as dilators 14a-14b, is attached to the distal end 122a of the elastic member 122. Any suitable dilator may be used, and the dilator may be attached to the elastic member 122 using any suitable method, including knotting, suturing, gluing, head-sealing, and molding. In certain embodiments, the dilator is a soft tissue anchor for securing the sling assembly in patient tissue. Exemplary soft tissue anchors are known in the art and disclosed, for example, in U.S. patent application "Systems, Devices, and Methods for Treating Pelvic Floor Disorders," Ser. No. 11/400,111, filed Apr. 6, 2006, which is incorporated herein by reference in its entirety.

According to one feature, the elastic member 122 is elongatable. After elongating the elastic member 122, upon release of pressure, the elastic member 122 may return to its original length. Alternatively, the elastic member 122 may retain its elongated length, and may not retract.

Figure 5:
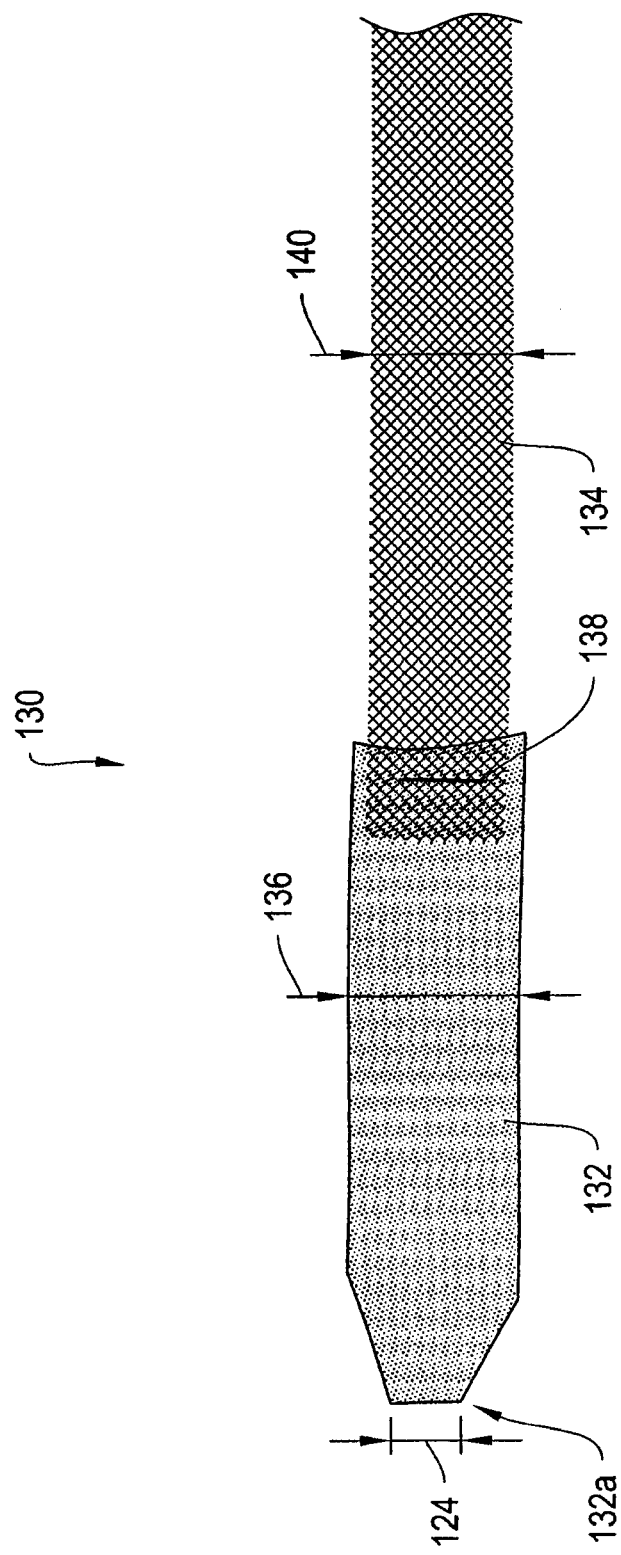
FIG. 5 is a top view of one end of a sling assembly, including an elastic member coupled to a sling, according to an alternative illustrative embodiment of the invention.

FIG. 5 is a top view of one end of a sling assembly 130, including an alternative elastic member 132 coupled to a mesh sling 134, according to an illustrative embodiment of the invention. The elastic member 122 is a single piece of elastic, having a width 136 about the same as or slightly greater than the width 140 of the sling 134. The elastic member 132 is attached to the sling 134 with a suture 138. However, in alternative embodiments, the elastic member may be attached to the sling using any suitable method, including suturing, gluing, heat-sealing, and molding.

According to one illustrative feature, the elastic member 132 tapers at the distal end 132a, such that the width 142 of the distal end 132a is about half the width 136 of the center of the elastic member 132. According to other embodiments, the distal end may have any suitable width, including a width that is less than or equal to the width of the center of the elastic member. The distal end 132a may taper to a point. In further embodiments, the elastic member 132 may be tapered in any suitable manner to form a selected shape of the distal end 132a, such as trapezoidal, hemispherical, oval, rounded, triangular, rectangular, or any other suitable shape. According to various embodiments, a dilator or other soft tissue anchor, such as dilators 14a-14b, is attached to the distal end 132a of the elastic member 132. Any suitable dilator or anchor may be used, and the dilator or anchor may be attached to the elastic member 132 using any suitable method, including suturing, gluing, head-sealing, and molding.

According to one feature, the elastic member 132 is elongatable. After elongating the elastic member 132, upon release of pressure, the elastic member 132 may return to its original length. Alternatively, the elastic member 132 may retain its elongated length, and may not retract.

Figure 6:
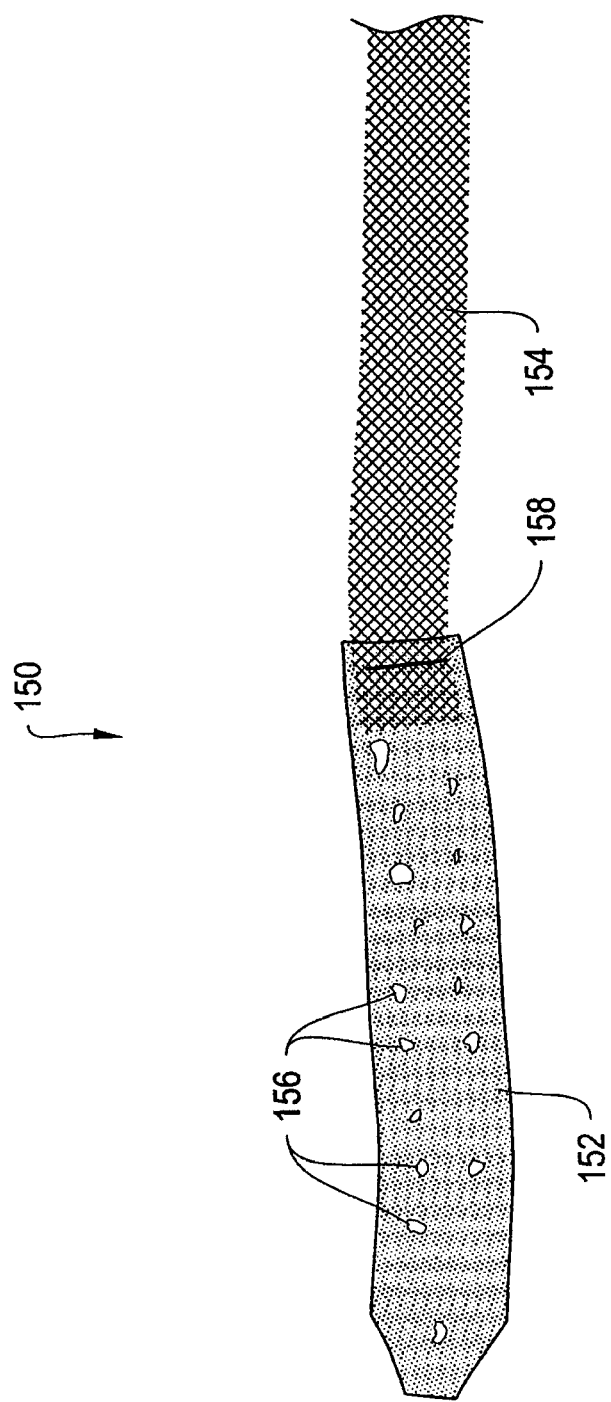
FIG. 6 is a top view of one end of a sling assembly, including an elastic member coupled to a sling, according to another illustrative embodiment of the invention.

FIG. 6 is a top view of one end of a sling assembly 150, including an elastic member 152 coupled to a sling 154, according to another illustrative embodiment of the invention. The elastic member 152 is attached to the sling 154 with a suture 158. However, in alternative embodiments, the elastic member may be attached to the sling using any suitable method, including suturing, gluing, heat-sealing, and molding. The elastic member 152 is substantially similar to the elastic member 132, but the elastic member 152 includes a plurality of apertures 156. According to one feature, the apertures 156 allow tissue to grow through the elastic member following implantation. The apertures may also anchor the sling in soft tissue following implantation. The apertures 156 may be any suitable size, and may have a width or a length of between about 0.01 cm, and about 0.5 cm, such as about 0.01 cm, about 0.03 cm, about 0.05 cm, about 0.08 cm, about 0.1 cm, and about 0.2 cm. According to a further embodiment, the apertures 156 may also be any suitable shape, such as circular, elliptical, square, rectangular, triangular, polygonal, or irregularly shaped.

Figures 7A, 7B:
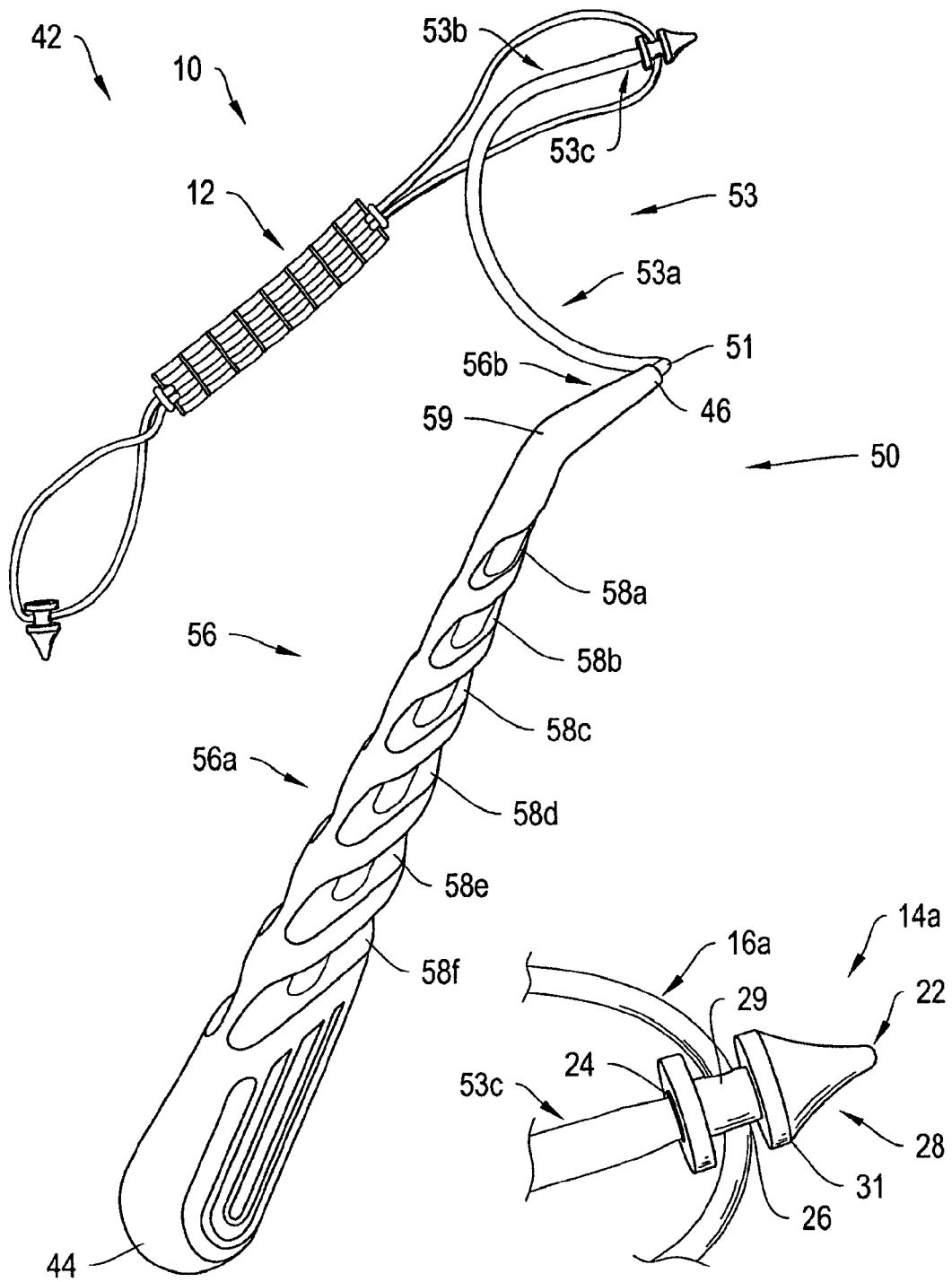
FIG. 7A shows a delivery system including a delivery device having a handle and a shaft, the shaft having a curved section extending in a plane different from a plane of the handle, and a sling assembly having a dilator/anchor interfitted over a distal end of the delivery device shaft according to an illustrative embodiment of the invention.
FIG. 7B depicts an enlarged view of the distal tip of the delivery device shaft of FIG. 7A interfitted with the dilator/anchor of the sling assembly.

Particular illustrative delivery devices and systems for implanting the above described sling assemblies will now be discussed with reference to FIGS. 7A-9. More specifically, FIGS. 7A and 7B show a delivery system 42 for delivering a sling assembly of the invention to an anatomical location in the body of a patient according to an illustrative embodiment of the invention. As described in further detail below with respect to FIGS. 11A-11C, the delivery system 42 is particularly configured for placement of the anchor/dilators 14a and 14b in or near respective transobturator membranes.

The delivery device 42 includes a handle 56 with first 56a and second 56b substantially straight sections located substantially in a first plane and angled relative to each other at 59, a transitional portion 51 extending out of a distal end 46 of the handle 56, and a shaft 53 extending from a distal end of the transitional portion 51. The shaft 53 includes a curved section 53a, a straight section 53b, and terminates in a conical tip 53c.

The transitional portion 51 interfits and extends axially out of the distal end 46 of the second handle section 56b to affix the shaft 53 to the handle 56. As a result, the transitional portion 51 is substantially co-planar with the handle 56 in the first plane. The curved section 53a of the shaft 53 is located in a second plane substantially orthogonal to the plane of the handle 56, and extends from a distal end of the transitional portion 51 first away from and then back toward the plane of the handle 56. The straight section 53b of the shaft 53 extends from a distal end of the curved section 53a back through the plane of the handle 56. The curved section 53a and the straight section 53b are substantially coplanar in the second plane. As mentioned above, according to the illustrative embodiment, the first and second planes are substantially orthogonal to each other. However, the first and second planes may be at any suitable angle (e.g., about 10, 20, 30, 45, 60, 70 or 80 degrees) to each other. In another illustrative embodiment, the first and second sections 56a and 56b of the handle 56 are at an angle of about 150 degrees to each other. However, the first and second sections 56a and 56b of the handle 56 may be at any suitable angle (e.g., about 80, 90, 100, 110, 120, 130, 140, 160, 170 or 180 degrees) to each other.

To provide structural reinforcement, the sections 56a and 56b have a cross-sectional diameter that tapers to be smaller at the distal end 46 of the handle 56. Additionally, rather than the handle section 56b being tapered, in other illustrative embodiments, the transitional portion 51 may be tapered. In other illustrative embodiments, rather than being formed as part of the shaft 53, the transitional portion 51 may instead be formed as part of the handle 56. Preferably, in operation, neither the handle 56 nor the transitional portion 51 extends into the body of the patient, and the angle between the transitional portion 51 and the shaft 53 provides a positive stop against this occurring.

According to the illustrative embodiment, the shaft 53 is formed from surgical grade stainless steel and the handle 56 is formed from a polymer plastic. However, any suitable materials may be employed for both. According to another feature of the illustrative embodiment, the handle 56 includes a plurality of laterally extending grooves/indentations 58a-58f for providing an improved grip for the medical operator.

The sling assembly 10 of FIGS. 7A and 7B is of the same type described above with respect to FIGS. 1A and 1B. However, in alternative illustrative embodiments, any of the sling assemblies of the invention may be employed with the delivery device 50. As shown in FIGS. 7A and 7B, the axially extending channel 24 of the anchor/dilator 14a interfits over the conical distal tip 53c of the shaft 53. As described below in more detail with respect to FIGS. 11A-11C, subsequent to implanting the anchor/dilator 14a, the device 50 is removed from the patient's body, and either delivery device 50 or another suitable delivery device is used to implant the anchor/dilator 14b to complete placement of the sling assembly 10.

FIGS. 8A and 8B show a delivery system 60 according to another illustrative embodiment of the invention. The delivery system 60 includes a delivery device 62 and the sling assembly 10. As in the case of the delivery system 42, the sling assembly 10 is of the same type described above with respect to FIGS. 1A and 1B. However, any sling assembly of the invention may be employed. As also in the case of the delivery system 42, the delivery device 62 is particularly suited for delivering the anchor/dilators 14a and 14b to locations near or within respective transobturator membranes.

The illustrative delivery device 62 includes a handle 64, a shaft 68, and a transitional portion 66 extending distally between a distal end 64a of the handle 64 and a proximal end 68a of the shaft 68. The transitional portion 66 includes a first straight section 66a, a curved section 66b, and a second straight section 66c, all lying substantially in a single plane, and may be formed as either part of the shaft 66 or as part of the handle 64. The shaft 68 includes a curved section 68b, a straight section 68c and a reduced diameter section 68d, all lying substantially in the same plane as the transitional portion 66.

In the illustrative embodiment, the first straight section 66a of the transitional portion 66 attaches to the distal end 64a of the handle 64, extends distally along a first axis 70, and preferably has a substantially constant outside diameter. The curved section 66b of the transitional portion 66 extends from a distal end of the first straight section 66a, curves away from the first axis 70, and also preferably has a substantially constant outer diameter. The second straight section 66c extends from a distal end of the curved section 66b along a second axis 72, and preferably has an outside diameter that decreases from its proximal end to its distal end to provide increased structural stability to the shaft 68. The curved section 68b of the shaft 68, preferably, has a substantially constant outer diameter, smaller than the out side diameter of the curved section 66b of the transitional portion 66, and extends from the distal end of the second straight section 66c of the transitional portion 66, curves back toward the first axis 70, and terminates at a distal end approximately at an intersection with the first axis 70. The straight section 68c, preferably, has a substantially constant outside diameter and extends from the distal end of the curved section 68b along a third axis 74, which crosses the first axis 70. According to the illustrative embodiment, the reduced diameter section 68d of the shaft 68 extends distally from the straight section 68c and is sized and shaped for fitting into the channel 24 of the anchor/dilators 14a and 14b.

As in the case of the delivery system 42, subsequent to implanting the anchor/dilator 14a, the device 62 is removed from the patient's body, and either delivery device 62 or another suitable delivery device is used to implant the anchor/dilator 14b to complete placement of the sling assembly 10.

Figures 9A, 9B:
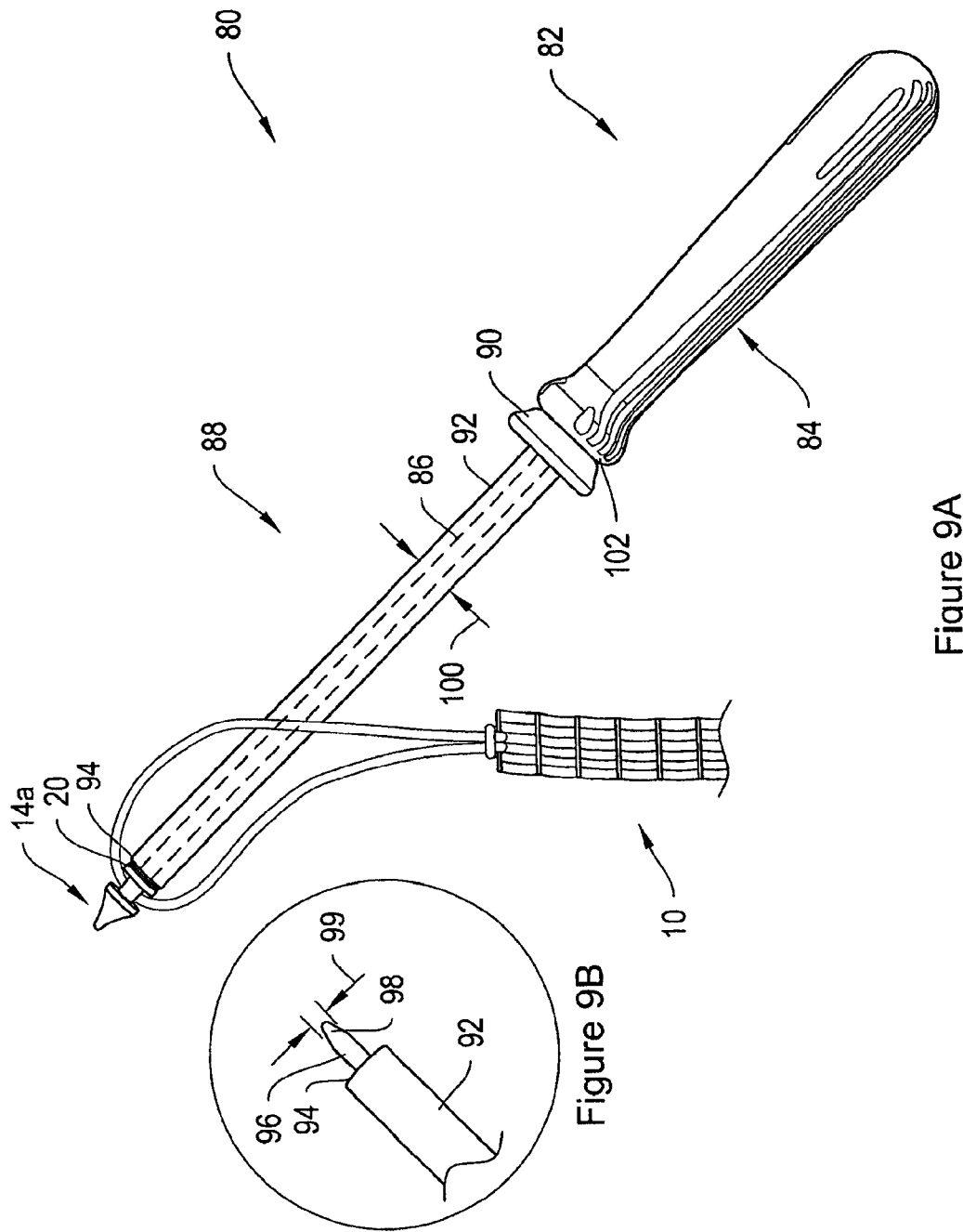
FIGS. 9A and 9B show a delivery system including a sling assembly interfitted onto a distal tip of a delivery device including a pusher assembly according to an illustrative embodiment of the invention.

FIGS. 9A and 9B show a delivery system 80 according to another illustrative embodiment of the invention. The delivery system 80 includes a delivery device 82 and the sling assembly 10. As in the case of the delivery system 42, the sling assembly 10 is of the same type described above with respect to FIGS. 1A and 1B. However, any sling assembly of the invention may be employed. In contrast to the delivery devices 50 and 62, the delivery device 82 is particularly suited for delivering the anchor/dilators 14a and 14b to locations in the abdomen other than at or near the transobturator membranes. However, in alternative illustrative embodiments, they may be suitably curved for such delivery.

The illustrative delivery device 82 includes a handle 84, a shaft 86 extending distally from the handle 84 and a pusher assembly 88 slidably interfitted over the shaft 86. The pusher assembly 88 includes a user actuator 90 at its handle end, and a push tube 92 which extends axially over the shaft 86 and terminates at a distal end 94. When retracted, the pusher assembly 88 exposes a distal portion 96 of the shaft 86. When extended, the distal end 94 of the pusher assembly 88 extends over the distal portion 96 of the shaft 86.

The depicted shaft 86 is substantially straight and terminates at a distal conical tip 98. However, in alternative embodiments, the shaft 86 may employ a distal tip sufficiently pointed or sharp to pierce through body tissue, or in other alternative embodiments employ a blunt tip. Additionally, the shaft 86 may have one or more curved portions. The shaft 86 is depicted as lying in substantially one plane. However, in alternative embodiments, the shaft 86 may have portions lying in more than one plane.

As shown, the axially extending channel 24 of the dilator/anchor 14a slidably interfits over the distal portion 96 of the shaft 86 so that the proximal end 20 of the dilator/anchor 14a abuts the distal end 94 of the push tube 92. According to the illustrative embodiment, the distal end 94 of the push tube 92 forms a shoulder around the shaft 86 and impedes the dilator/anchor 14a of the sling assembly 10 from sliding proximally along the length of the shaft 86.

In operation, the distal end of the delivery device 82 with the dilator/anchor 14a so installed is inserted into the body of the patient. When the desired location is reached, the medical operator slides the pusher assembly 88 distally causing the shoulder formed by the distal end 94 of the push tube 92 to engage the proximal end 20 of the dilator/anchor 14a to push the dilator/anchor 14a off the distal end 96 of the shaft 86.

According to the illustrative embodiment, with the pusher assembly 88 in a retracted position, the exposed distal section 96 of the shaft 86 is between about 2 centimeters and about 4 centimeters long. In other illustrative embodiments, it is between about 1 centimeter and about 3 centimeters long. In further illustrative embodiments, the distal section 96 of the shaft 86 has an outside diameter 99 of between about 0.03 inches and about 0.05 inches. In one illustrative embodiment, it has an outside diameter of about 0.04 inches. According to other configurations, the outside diameter 100 of the push tube 92 is between about 0.07 inches and about 0.1 inches. In one implementation, the outside diameter 100 is about 0.09 inches. According to one configuration, the total distance from the distal end 102 of the handle 84 to the distal-most tip 98 of the shaft 86 is between about 7 centimeters and about 20 centimeters.

FIG. 10 shows a pelvic floor implant 160 having a trapezoidal central region 160a, six arms 164a-164f, six elastic members 166a-166f, and anchor/dilators 14a-14f, according to an illustrative embodiment of the invention. In other embodiments the central region 160a may be rectangular, polygonal, or elliptical. In certain embodiments, the implant 160, including the arms 164a-164f, spans at least a length 162 that extends between or beyond a first obturator membrane and a second obturator membrane of the patient, also known as the patient's obturator-to-obturator length. Thus, when the elastic members 166a-166f are delivered via the single vaginal incision, the elastic members 166a-166c attach to a first obturator membrane either directly or via dilators 14a-14c directly coupled to the elastic members 166a-166c, and elastic members 166d-166f attach to the contralateral obturator membrane either directly or via dilators 14d-14f directly coupled to the elastic members 166d-166f, as illustrated with respect to FIGS. 1A-3. In various embodiments, the length 162 of the implant 160 is between about 5 cm and about 30 cm. For example, the implant 160 may have a length 162 of about 5 cm, about 7 cm, about 10 cm, about 12 cm, about 15 cm, about 20 cm, or about 25 cm, and thus be sized to span the patient's full obturator-to-obturator length and directly couple to soft tissue anchors that anchor in respective obturator membranes with no intervening filament. In one embodiment, the length 162 is shorter than the obturator-to-obturator length, and the length from dilators 14a-14c to dilators 14d-14f is about equal to or greater than the obturator-to-obturator length.

In alternative implementations, the elastic members 166a-166f are secured to other target tissue regions in the patient's retropubic space, such as the patient's sacrospinous ligaments or levator ani muscles. By way of example, elastic members 166a and 166d may extend to target regions of the sacrospinous ligament, elastic members 166b and 166e may extend to target regions near the tendinous arch of the levator ani muscle, and elastic members 166c and 166f may extend to target regions of the obturator membranes. Each of the elastic members 166a-166f may have varying lengths in order to reach their respective target tissue regions.

According to one embodiment, the implant 160 has an anterior-to-posterior length of between about 2.5 centimeters and about 8 centimeters, which allows the implant 160 to extend under and provide hammock-like support to posterior regions of the pelvic region, including, for example, the base of the bladder. In general, the implant 160 may have any desired anterior-to-posterior length to support other anatomical regions of the pelvic floor. For example, the implant 160 may have an anterior-to-posterior length of between about 0.5 cm and about 2 cm and may be suitable to support one or both of the patient's urethra and bladderneck. Alternatively, implant 160 may have an anterior-to-posterior length of greater than about 3 cm, greater than about 5 cm, greater than about 7 cm, or greater than about 10 cm to support the patient's urethra, bladderneck, and/or bladder.

According to the illustrative embodiment, the posterior elastic members 166a and 166d form an elastic loop comprising one elastic strand. The elastic loop of elastic members 166a and 166d is interwoven across the length 162 of the implant 160, through arms 164a and 164d. The elastic loop of elastic members 166a and 166d may be longer than the length 162 of the implant 160, with the elastic members 166a and 166d extending beyond the arms 164a and 164d. The elastic loop of elastic members 166a and 166d, and the elastic loop of elastic members 166c and 166f, may be substantially similar to the elastic member 34 of FIG. 2.

In the illustrative embodiment, elastic members 166b and 166e are attached to arms 164b and 164e and dilators 14b and 14e. The elastic members 166b and 166e may be attached to arms 164b and 164e and dilators 14b and 14c in substantially the same manner as elastic members 16a and 16b of FIG. 1. According to the illustrative embodiment, the elastic members 166a-166f have a closed loop form. In other embodiments, the elastic members 166a-166f of the pelvic floor implant 160 may comprise a single strand of elastic, such as elastic members 122, 132, and 152 of FIGS. 4, 5, and 6, respectively. In some embodiments, the elastic members 166a-166f may comprise a single strand of elastic including apertures that directly secure one or more of the elastic members 166a-166f to a target tissue region, such as the elastic member 152 of FIG. 6.

In an alternative example, the pelvic floor implant 160 includes four (4) elastic member. In this example, the central portion may be any suitable shape, including square, rectangular, trapezoidal, polygonal, and elliptical, and the elastic members may be attached to any suitable location on the central portion, such as at corners of the central portion.

Figure 11A:
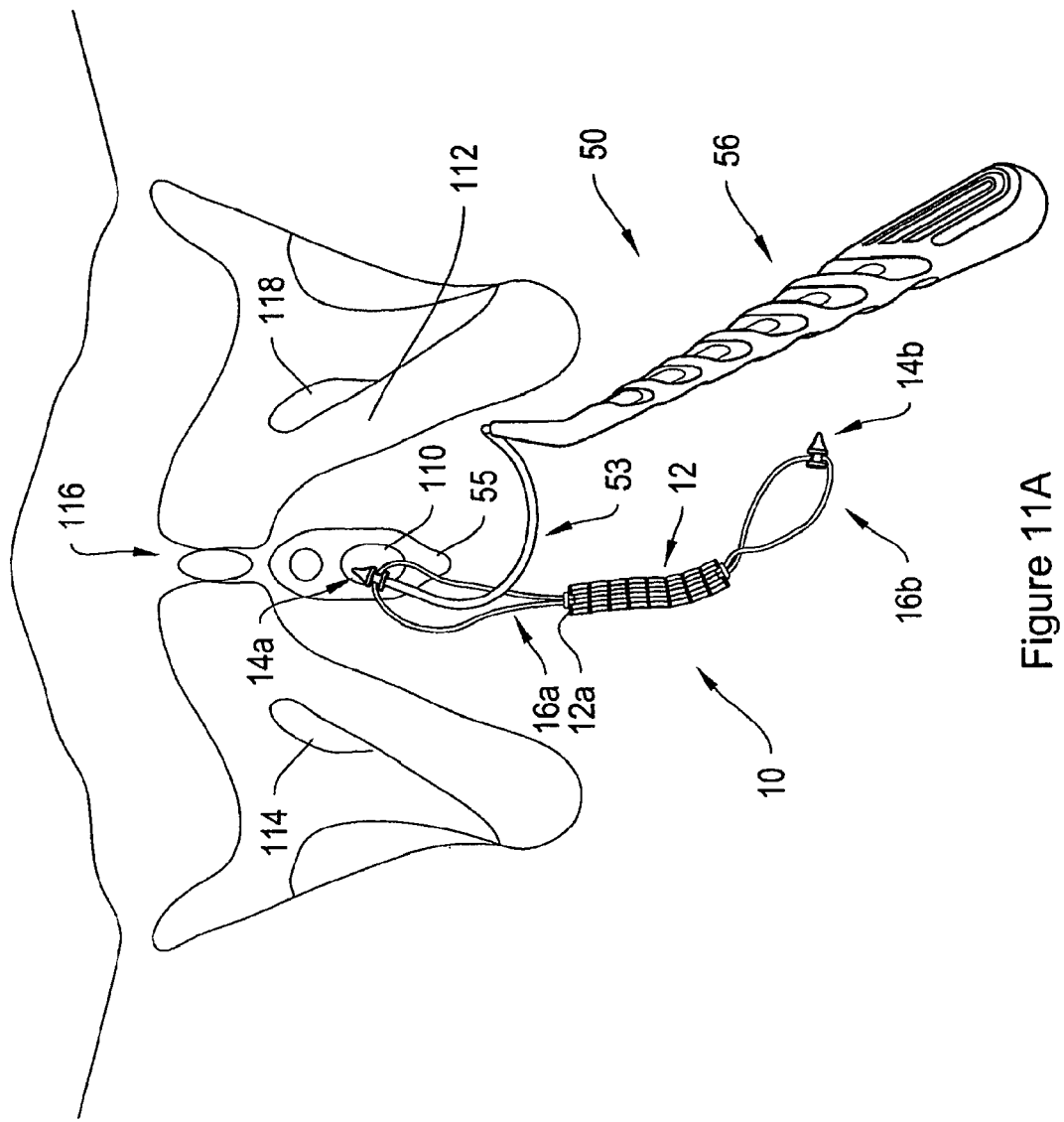
FIGS. 11A-11C depict an exemplary approach for delivering a sling assembly to an anatomical site in the body of a patient using a delivery system of the invention.
Figure 11B:
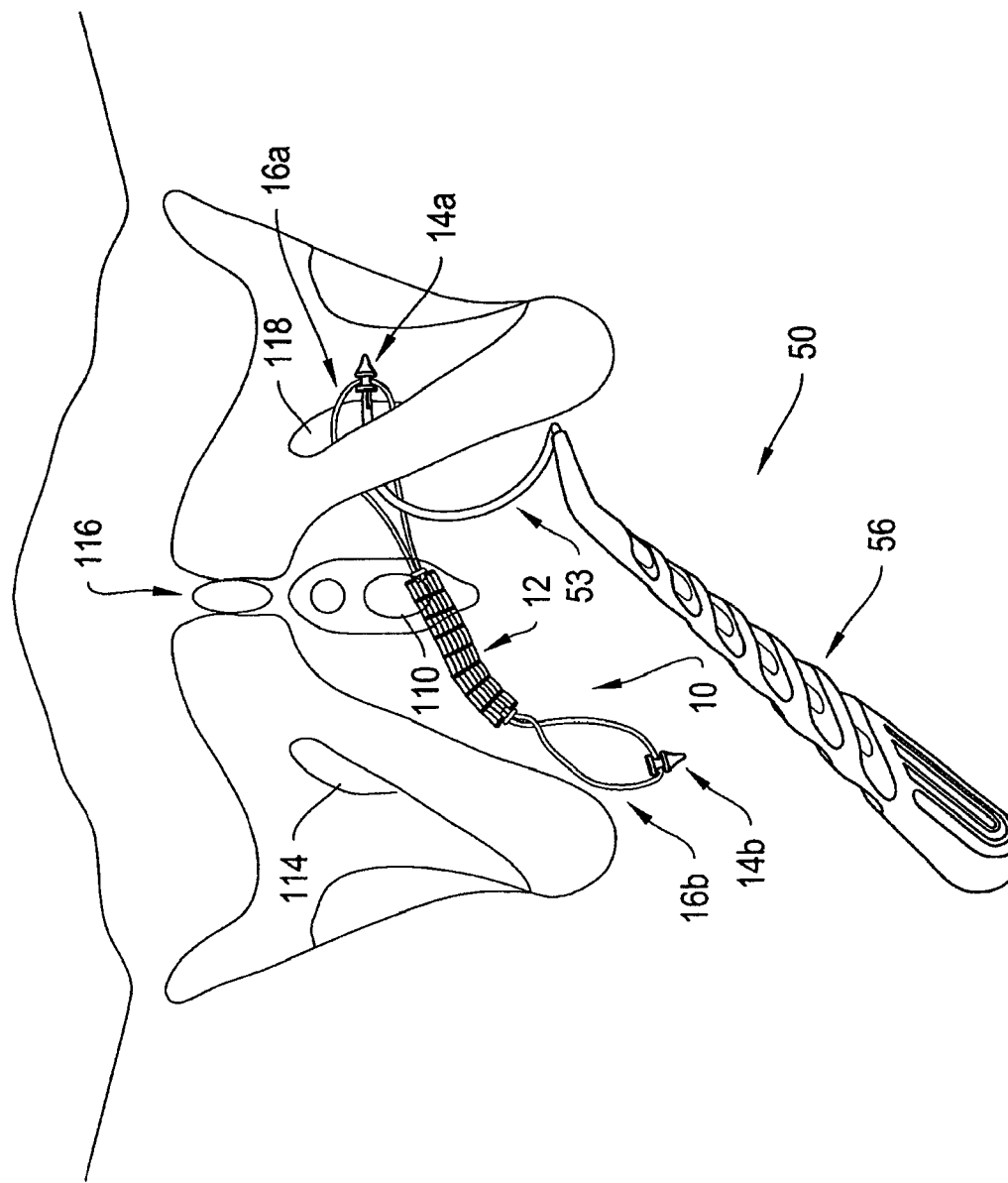
Figure 11C:
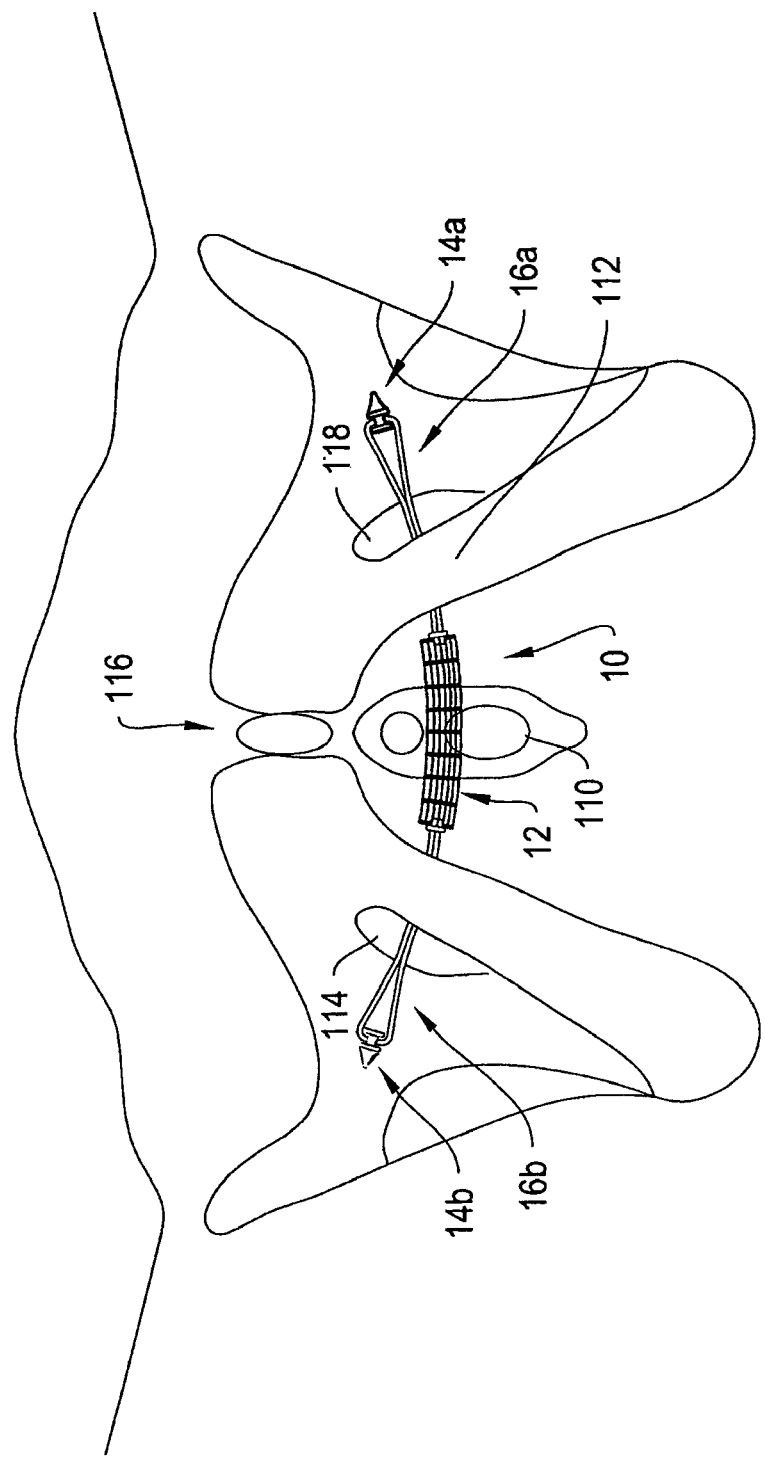

FIGS. 11A-11C depict an approach for delivering the sling assembly 10 transobturally using the delivery system 42 of FIGS. 7A and 7B according to an illustrative embodiment of the invention. The pelvic floor implant 160 of FIG. 10 may also be delivered according to this approach. The delivery device 50 is employed to describe this embodiment. However, the delivery device 62 or a suitably curved version of the delivery device 82 may be employed in a similar fashion.

In an exemplary surgical technique, a patient is placed on an operating table in a position to provide access to the pelvic region. The operator may subject the patient to local anesthesia, regional anesthesia, and/or general anesthesia or sedation according to his preference. Next, the operator makes a transverse incision (not shown) in the anterior vaginal wall 110 of the patient and dissects the incision bilaterally according to his preference using, for example, surgical scissors. In certain implementations, the operator dissects bilaterally to the interior portion of the inferior pubic ramus on both sides of the patient. The operator then identifies a path of delivery of the implant by palpating tissue of the pelvic region. The operator may palpate by inserting his finger through the vaginal incision and may identify anatomical structures such as the obturator foramen.

Next, the operator accesses the patient's pelvic region via the transverse incision to insert an implant into the patient's pelvic region and secure the implant within the region so that at least a portion of the implant is located posterior to the bladderneck. To accomplish this, the operator first provides an implant, such as those described herein, having an elastic member that connects an anchor 14a to the implant. The operator then couples the anchor 14a, attached to the sling end 12a via elastic member 16a, to the distal portion 53c of the delivery device shaft 53. Referring to FIGS. 11A and 11B, the operator grasps the handle 56 and inserts the delivery device shaft portion 53c with the anchor 14a installed into the body through the external vaginal opening and then guides the end of the shaft 53c through the vaginal incision towards an obturator membrane 118. This elongates the elastic member 16a and the anchor 14a within the patient. With a lateral motion, the medical operator passes the curved portion 53a of the shaft 53 behind the ischiopubic ramus 112 and pierces the obturator membrane 118, further elongating the elastic member 16a. The delivery device shaft 53 can then be withdrawn from the body leaving the anchor 14a implanted near, in or through the obturator membrane 118 and, optionally, fixed to the obturator membrane 118. In certain embodiments, the elastic member 16a retracts after implantation, while in other embodiments, the elastic member 16a remains in its elongated state.

The operator may palpate during delivery as preferred. The operator may also use the posterior portion of the patient's pubic bone as an anatomical landmark to assist in guiding the needle. The operator optionally secures the implant 10 against the shaft 53 during delivery so that the implant 10 does not obstruct the operator's vision or the path of delivery, using any suitable sterile securing means, such as a sterile elastic band or tie.

The operator punctures the obturator membrane 118 with the dilator 14a. In certain embodiments, the operator stops short of extending a portion of the dilator 14a or shaft 53 through the surface of the patient's skin in the groin. The location of the puncture within the obturator membrane 118 depends on the desired location of the dilator/anchor being delivered. For example, the operator may deliver dilator 14a through a sufficiently posterior region of the obturator membrane 118 so that the implant assembly 10 extends to posterior regions of the patient's pelvic floor and provides posterior support, or he may deliver the dilator 14a through an anterior region of the obturator membrane 118 so that the implant assembly 10 extends to and supports anterior regions of the patient's pelvic floor. In certain implementations, the operator generally delivers the implant 10 along a path that avoids certain pelvic structures, such as the internal pudendal artery, the pudendal canal, the perineal nerve, the labial nerve, and other vascular and nerve structures.

The operator may hear and/or feel a pop indicating that he has pierced the obturator membrane 118. The operator gauges the length from the vaginal incision to the obturator 118 by using the markings or indications (not shown) on the shaft 53, and/or by visually gauging the length from the proximal edge of the dilator 14a to the vaginal incision to assure that the length of the implant 10 is suitable for the patient. As mentioned above, in certain implementations, the implant 10 includes a visual marking that the operator places under a predetermined anatomical landmark, such as the urethra or the bladder.

In certain "single incision" embodiments, the operator does not advance the shaft 53 through the skin. Rather, the operator advances the shaft 53 to be near, contact, apply pressure to, poke ("tent-up"), or, in certain uses, pierce the epidermis (not shown) just beyond the obturator membrane 118, without penetrating entirely through the skin, until the shaft 53 is in an appropriate position to deliver the dilator 14a. The operator may externally palpate the epidermis proximal to the obturator membrane 118 to feel the shaft 53 poke the epidermis and confirm its location. In certain embodiments the operator stops extending the dilator 14a when it reaches a position that is beneath the patient's stratum corneum, while in other embodiments the operator stops the dilator 14a from extending to the epidermis. In certain embodiments the operator stops the dilator 14a in the subcutaneous tissue or beneath the subcutaneous and does not extend the dilator 14a to the dermal layer. In alternative "two incision" embodiments, the operator drives the shaft 53 through the skin in the patient's groin, then cuts the dilator and implant and, optionally, sutures the implant to the groin area.

In one embodiment, the operator advances an elastic member through the obturator foramen by piercing the obturator membrane. According to this embodiment, the elastic member is stretched for advancement through the obturator membrane, and, after the elastic member is released, it retracts to near its original length. As the elastic retracts, the friction between the elastic and the obturator membrane causes the elastic member to remain in place, through the obturator membrane. Thus, the elastic member may act as a soft tissue anchor. In another implementation, the elastic does not retract, but its surface still creates sufficient friction with respect to the obturator membrane to stay secure within the membrane.

In certain implementations, the incision is made in the vagina so as to allow the inserted shaft to be near, contact, apply pressure to, or poke the skin at a position that is generally in line with the urethral meatus. The operator anchors the dilator 14a to the obturator membrane 118, and retracts the shaft 53, thereby decoupling the shaft 53 from the dilator 14a, using methods discussed above. As indicated in FIG. 11C, this process is repeated with the same delivery device, or optionally, with a second delivery device having an opposite curvature, to implant the second anchor/dilator 14b near, in or through the obturator membrane 114 on the contralateral side of the body. As shown in FIG. 11C, the sling 12 forms a supportive platform under the urethra 116. With the sling assembly 10 so implanted, the elastic members 16a and 16b can stretch and contract to automatically adjust the length, and thus the tension, of the sling assembly 10. This also adjusts the pressure that the sling 12 asserts on the urethra. As mentioned above, such automatic adjustability allows the sling assembly 10 to adapt in real-time to patient movement, muscle flexure, and anatomical changes. Anatomical changes include, for example, body growth and/or shrinkage such as that due to aging, weight gain and weight loss.

Variations, modifications, and other implementations of what is described may occur without departing from the spirit and the scope of the invention. By way of example, and without limitation, examples of slings, sling assemblies, sling delivery devices and approaches, sling assembly-to-delivery device association mechanisms, and sling anchoring mechanisms including features that may be employed with the above described invention are disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," U.S. patent application Ser. No. 10/093,371, entitled "System for implanting an implant and method thereof," U.S. Pat. No. 6,911,003, entitled "Transobturator surgical articles and methods," U.S. patent application Ser. No. 10/840,646, entitled "Method and Apparatus for Cystocele Repair," U.S. application Ser. No. 10/834,943, entitled "Method and Apparatus for Treating Pelvic Organ Prolapse," U.S. patent application Ser. No. 10/804,718, entitled "Prolapse Repair," and U.S. patent application Ser. No. 11/115,655, entitled "Surgical Implants and Related Methods," U.S. patent application Ser. No. 11/400,111, entitled "Systems, Devices, and Methods for Treating Pelvic Floor Disorders," and U.S. patent application Ser. No. 11/399,913, entitled "Systems, Devices, and Methods for Sub-Urethral Support," the entire contents of all of which are incorporated herein by reference.

Another advantage of the above described invention is that it enables a medical operator to place a supportive sling under the bladder neck or the mid-urethra to provide a urethral platform, without requiring any incision other than those made in the vaginal wall. More particularly, employing the devices, systems, methods and features of the invention, a medical operator can place an implantable sling without making any abdominal or ischiopubic incisions.

It should be understood that for the described procedures, and other procedures using the described devices and systems, the delivery devices and sling and/or sling assembly may be tailored, for example, in the dimensions of the devices, such as length, diameter, shape, and curvature; sling assembly, such as length and width of the sling or suture thread; and for a particular method of delivery or for placement to a specific anatomical site.

What is claimed is:

1. A sling assembly comprising:
   an implantable sling having first and second ends and first and second longitudinal edges;
   first and second dilators, each having proximal and distal ends, an axially oriented passage extending at least partially from the distal end to the proximal end, the passage being sized and shaped for receiving a distal end of a delivery device shaft, and an aperture extending through each of the first and second dilators in a direction substantially perpendicular to the axially oriented passage; and
   an elastic member comprising a material capable of from a retracted state to an elongated state and substantially retracting to its former length, the elastic member being longer than the sling when in the retracted state, and extending axially through the sling, the first dilator being attached to a first end of the elastic member, and the second dilator being attached to a second end of the elastic member.

2. The sling assembly of claim 1, wherein at least one of the first and second dilators has a radially oriented through aperture located between the proximal and distal ends.

3. The sling assembly of claim 2, wherein the elastic member has a closed loop form, and extends through the radially oriented through aperture of at least one of the first and second dilators.

4. The sling assembly of claim 1, wherein at least one of the first dilator and the second dilator is a soft tissue anchor.

5. The sling assembly of claim 1, wherein the implantable sling includes one or more laterally extending filaments.

6. The sling assembly of claim 1, wherein the implantable sling is tanged.

7. The sling assembly of claim 1, wherein the implantable sling is de-tanged.

8. The sling assembly of claim 1, wherein the implantable sling is partially tanged.

9. A sling assembly comprising:
   an implantable mesh sling;
   first and second dilators, each having proximal and distal ends, an axially oriented passage extending at least partially from the distal end to the proximal end, the passage being sized and shaped for receiving a distal end of a delivery device shaft, and an aperture extending through each of the first and second dilators in a direction substantially perpendicular to the axially oriented passage, wherein at least one of the first and second dilators is a soft tissue anchor; and
   at least one elastic member comprising a material capable of stretching to an elongated state and substantially retracting to its former length, the at least one elastic member being attached to at least one of the first and second dilators.

10. The sling assembly of claim 9, wherein the implantable mesh sling further comprises one or more laterally extending filaments.

11. The sling assembly of claim 9, wherein the implantable mesh sling is about 5 cm to about 7 cm long.

12. The sling assembly of claim 9, wherein the implantable mesh sling is tanged.

13. The sling assembly of claim 9, wherein the implantable mesh sling is de-tanged.

14. The sling assembly of claim 9, wherein the implantable mesh sling is partially tanged.

15. The sling assembly of claim 9, wherein the implantable mesh sling further includes a centering means.

16. The sling assembly of claim 9, wherein the implantable mesh sling further includes a position indicating means.

17. The sling assembly of claim 9, wherein at least a portion of the sling assembly is biodegradable.

18. The sling assembly of claim 9, wherein:
   the implantable sling has a first end and a second end;
   the at least one elastic member is attached to the first dilator; and
   the second dilator is attached to the second end of the sling.

19. The sling assembly of claim 9, wherein:
   the at least one elastic member includes a first elastic member and a second elastic member;
   the first elastic member is attached to the first dilator and a first end of the implantable sling; and
   the second elastic member is attached the second dilator and a second end of the implantable sling.

20. The sling assembly of claim 9, wherein the at least one elastic member has a closed loop form, and extends through the aperture of at least one of the first dilator and the second dilator.

* * * * *